US008021368B2

(12) United States Patent
Haines

(10) Patent No.: US 8,021,368 B2
(45) Date of Patent: Sep. 20, 2011

(54) METHODS AND APPARATUS FOR IMPROVED CUTTING TOOLS FOR RESECTION

(75) Inventor: Timothy G. Haines, Seattle, WA (US)

(73) Assignee: Hudson Surgical Design, Inc., Seattle, WA (US)

( * ) Notice: Subject to any disclaimer, the term of this patent is extended or adjusted under 35 U.S.C. 154(b) by 1516 days.

(21) Appl. No.: 11/075,842

(22) Filed: Mar. 8, 2005

(65) Prior Publication Data

US 2006/0015109 A1 Jan. 19, 2006

Related U.S. Application Data

(63) Continuation-in-part of application No. 11/036,584, filed on Jan. 14, 2005, and a continuation-in-part of application No. 11/049,634, filed on Feb. 2, 2005, now abandoned.

(60) Provisional application No. 60/551,307, filed on Mar. 8, 2004, provisional application No. 60/551,080, filed on Mar. 8, 2004, provisional application No. 60/551,078, filed on Mar. 8, 2004, provisional application No. 60/551,096, filed on Mar. 8, 2004, provisional application No. 60/551,631, filed on Mar. 8, 2004, provisional application No. 60/551,262, filed on Mar. 8, 2004, provisional application No. 60/551,160, filed on Mar. 8, 2004, provisional application No. 60/536,320, filed on Jan. 14, 2004, provisional application No. 60/540,992, filed on Feb. 2, 2004.

(51) Int. Cl.
*A61B 17/58* (2006.01)
*A61B 17/60* (2006.01)
*A61F 2/00* (2006.01)

(52) U.S. Cl. ............... 606/88; 606/82; 606/87

(58) Field of Classification Search .............. 606/82, 606/87, 88
See application file for complete search history.

(56) References Cited

U.S. PATENT DOCUMENTS 2,697,433 A 12/1954 Zehnder
(Continued)

FOREIGN PATENT DOCUMENTS

EP 0104732 4/1984
(Continued)

OTHER PUBLICATIONS

T.D.V. Cooke et al., *Universal Bone Cutting Device for Precision Knee Replacement Arthroplasty and Osteotomy*, 7 J. Biomed. Eng'g 45, 47, col. 2, ll. 52-57 (1985).

(Continued)

*Primary Examiner* — Thomas C Barrett
*Assistant Examiner* — Andrew Yang
(74) *Attorney, Agent, or Firm* — Patterson Thuente Christensen Pedersen, P.A.

(57) ABSTRACT

A cutting tool is provided with an arcuate cutting blade that preferably engages a guide tool to create a curved resected surface during an arthorplasty procedure. In one embodiment, a depth of the cutting blade is sufficient to permit the simultaneous creation of resected surfaces on two bones that articulate, such as both the femur and the tibia for a given condyle, without the need to reposition the guide or the leg. In another embodiment, a cutting member has a generally rectangular cross-section along a longitudinal axis with a first and second surface having cutting teeth defined thereon and a third and fourth surface adapted to interface with a cutting guide positioned proximate the bone. In this embodiment, the cutting tool can resect the bone in two different directions without reorienting the cutting member.

22 Claims, 36 Drawing Sheets

U.S. PATENT DOCUMENTS

| | | |
|---|---|---|
| 3,457,922 A | 7/1969 | Ray |
| 3,739,662 A | 6/1973 | Windelman et al. |
| 3,748,662 A | 7/1973 | Helfet |
| 3,774,244 A | 11/1973 | Walker |
| 3,798,679 A | 3/1974 | Ewald |
| 3,816,855 A | 6/1974 | Salch |
| 3,906,550 A | 9/1975 | Rostoker |
| 3,943,934 A | 3/1976 | Bent |
| 3,953,899 A | 5/1976 | Charnley |
| 3,958,278 A | 5/1976 | Lee |
| 3,977,289 A | 8/1976 | Tuke |
| 4,000,525 A | 1/1977 | Klawitter |
| 4,016,606 A | 4/1977 | Murray |
| 4,069,824 A | 1/1978 | Weinstock |
| 4,178,641 A | 12/1979 | Gruendel |
| 4,207,627 A | 6/1980 | Cloutier |
| 4,213,209 A | 7/1980 | Insall |
| 4,249,270 A | 2/1981 | Bahler |
| 4,340,978 A | 7/1982 | Buechel |
| 4,349,058 A | 9/1982 | Comparetto |
| 4,353,135 A | 10/1982 | Forte |
| 4,358,859 A | 11/1982 | Schurman et al. |
| 4,421,112 A | 12/1983 | Mains |
| 4,457,307 A | 7/1984 | Stillwell |
| 4,474,177 A | 10/1984 | Whiteside |
| 4,479,271 A | 10/1984 | Bolesky |
| 4,487,203 A | 12/1984 | Androphy |
| 4,501,266 A | 2/1985 | McDaniel |
| 4,502,483 A | 3/1985 | Lacey |
| 4,524,766 A | 6/1985 | Petersen |
| 4,566,448 A | 1/1986 | Rohr, Jr. |
| 4,567,886 A | 2/1986 | Petersen |
| 4,568,348 A | 2/1986 | Johnson et al. |
| 4,584,999 A | 4/1986 | Arnegger |
| 4,586,496 A | 5/1986 | Keller |
| 4,586,933 A | 5/1986 | Shoji et al. |
| 4,653,488 A | 3/1987 | Kenna |
| 4,659,331 A | 4/1987 | Matthews |
| 4,662,889 A | 5/1987 | Zichner |
| 4,693,721 A | 9/1987 | Ducheyne |
| 4,703,751 A | 11/1987 | Pohl |
| 4,709,699 A | 12/1987 | Michael |
| 4,711,639 A | 12/1987 | Grundei |
| 4,714,472 A | 12/1987 | Averill |
| 4,714,473 A | 12/1987 | Bloebaum |
| 4,718,413 A | 1/1988 | Johnson |
| 4,721,104 A | 1/1988 | Kaufman |
| 4,722,330 A | 2/1988 | Russell |
| 4,731,086 A | 3/1988 | Whiteside |
| 4,736,086 A | 4/1988 | Obara |
| 4,736,737 A | 4/1988 | Fargie |
| 4,738,256 A | 4/1988 | Freeman |
| 4,759,350 A | 7/1988 | Dunn |
| 4,770,663 A | 9/1988 | Hanslik |
| 4,787,383 A | 11/1988 | Kenna |
| 4,808,185 A * | 2/1989 | Penenberg et al. ........ 623/20.29 |
| 4,822,365 A | 4/1989 | Walker |
| 4,834,758 A | 5/1989 | Lane |
| 4,841,975 A | 6/1989 | Woolson |
| 4,880,429 A | 11/1989 | Stone |
| 4,892,093 A | 1/1990 | Zarnowski |
| 4,893,619 A | 1/1990 | Dale |
| 4,896,663 A | 1/1990 | Vandewalle |
| 4,919,667 A | 4/1990 | Richmond |
| 4,926,847 A | 5/1990 | Luckman |
| 4,935,023 A | 6/1990 | Whiteside |
| 4,936,853 A | 6/1990 | Fabian |
| 4,938,762 A | 7/1990 | Wehrli |
| 4,938,769 A | 7/1990 | Shaw |
| 4,944,757 A | 7/1990 | Martinez |
| 4,950,298 A | 8/1990 | Gustilo |
| 4,952,213 A | 8/1990 | Bowman |
| 4,963,152 A | 10/1990 | Hofmann |
| 4,971,075 A | 11/1990 | Lee |
| 4,979,949 A | 12/1990 | Matsen |
| 4,986,833 A | 1/1991 | Worland |
| 5,002,545 A | 3/1991 | Whiteside |
| 5,002,547 A | 3/1991 | Poggie |
| 5,007,933 A | 4/1991 | Sidebotham |
| 5,007,934 A | 4/1991 | Stone |
| 5,021,056 A | 6/1991 | Hofman |
| 5,021,061 A | 6/1991 | Wevers |
| 5,032,134 A | 7/1991 | Lindwer |
| 5,041,138 A | 8/1991 | Vacanti |
| 5,047,032 A | 9/1991 | Jellicoe |
| 5,049,149 A | 9/1991 | Schmidt |
| 5,053,037 A | 10/1991 | Lackey |
| 5,059,037 A | 10/1991 | Albert |
| 5,062,852 A | 11/1991 | Dorr |
| 5,080,675 A | 1/1992 | Lawes |
| 5,092,869 A | 3/1992 | Warsaw |
| 5,098,436 A | 3/1992 | Ferrante |
| 5,100,409 A | 3/1992 | Coates |
| 5,108,398 A | 4/1992 | McQueen |
| 5,112,336 A | 5/1992 | Krevolin |
| 5,116,375 A | 5/1992 | Hofmann |
| 5,122,144 A | 6/1992 | Bert |
| 5,129,909 A | 7/1992 | Sutherland |
| 5,133,758 A | 7/1992 | Hollister |
| 5,133,759 A | 7/1992 | Turner |
| 5,147,365 A | 9/1992 | Whitlock |
| 5,147,405 A | 9/1992 | Van Zile |
| 5,176,710 A | 1/1993 | Hahn |
| 5,178,626 A | 1/1993 | Pappas |
| 5,190,547 A | 3/1993 | Barber, Jr. |
| 5,197,944 A | 3/1993 | Steele |
| 5,201,881 A | 4/1993 | Evans |
| 5,203,807 A | 4/1993 | Evans |
| 5,206,023 A | 4/1993 | Hunziker |
| 5,219,362 A | 6/1993 | Tuke |
| 5,226,916 A | 7/1993 | Goodfellow |
| 5,228,459 A | 7/1993 | Caspari |
| 5,234,432 A | 8/1993 | Brown |
| 5,234,433 A | 8/1993 | Bert |
| 5,236,432 A | 8/1993 | Matsen |
| 5,236,461 A | 8/1993 | Forte |
| 5,236,875 A | 8/1993 | Trigg |
| 5,250,050 A | 10/1993 | Poggie |
| 5,263,498 A | 11/1993 | Caspari |
| 5,263,956 A | 11/1993 | Nobles |
| 5,269,786 A | 12/1993 | Morgan |
| 5,275,603 A | 1/1994 | Ferrante |
| 5,279,575 A | 1/1994 | Sugarbaker |
| 5,282,803 A | 2/1994 | Lackey |
| 5,282,867 A | 2/1994 | Mikhail |
| 5,284,482 A | 2/1994 | Mikhail |
| 5,304,181 A | 4/1994 | Caspari |
| 5,306,276 A | 4/1994 | Johnson |
| 5,314,482 A | 5/1994 | Goodfellow |
| 5,326,358 A | 7/1994 | Aubriot |
| 5,330,533 A | 7/1994 | Walker |
| 5,330,534 A | 7/1994 | Herrington |
| 5,342,368 A | 8/1994 | Petersen |
| 5,358,527 A | 10/1994 | Forte |
| 5,358,529 A | 10/1994 | Davidson |
| 5,358,531 A | 10/1994 | Goodfellow |
| 5,364,401 A | 11/1994 | Ferreante |
| 5,364,402 A | 11/1994 | Mumme |
| 5,370,699 A | 12/1994 | Hood |
| 5,370,701 A | 12/1994 | Fin |
| 5,391,170 A | 2/1995 | McGuire |
| 5,405,349 A | 4/1995 | Burkinshaw |
| 5,413,604 A | 5/1995 | Hodge |
| 5,415,663 A | 5/1995 | Luckman |
| 5,417,694 A | 5/1995 | Marik |
| 5,417,695 A | 5/1995 | Axelson, Jr. |
| 5,443,464 A | 8/1995 | Russell |
| 5,454,816 A | 10/1995 | Ashby |
| 5,462,551 A | 10/1995 | Bailey |
| 5,470,335 A | 11/1995 | Du Toit |
| 5,474,559 A | 12/1995 | Bertin |
| 5,480,446 A | 1/1996 | Goodfellow |
| 5,514,136 A | 5/1996 | Richelsoph |
| 5,514,139 A | 5/1996 | Goldstein |
| 5,514,143 A | 5/1996 | Bonutti |
| 5,520,694 A | 5/1996 | Dance |
| 5,520,695 A | 5/1996 | Luckman |

| Patent No. | Date | Name |
|---|---|---|
| 5,540,695 A | 7/1996 | Levy |
| 5,542,947 A | 8/1996 | Treacy |
| 5,549,684 A | 8/1996 | Amino |
| 5,549,688 A | 8/1996 | Ries |
| 5,551,429 A | 9/1996 | Fitzpatrick |
| 5,562,674 A | 10/1996 | Stalcup |
| 5,569,262 A | 10/1996 | Carney |
| 5,571,100 A | 11/1996 | Goble |
| 5,578,039 A | 11/1996 | Vendrely |
| 5,593,411 A | 1/1997 | Stalcup |
| 5,597,379 A | 1/1997 | Haines |
| 5,601,563 A | 2/1997 | Burke |
| 5,601,566 A | 2/1997 | Dance |
| 5,609,645 A | 3/1997 | Vinciguerra |
| 5,611,802 A | 3/1997 | Samuelson |
| 5,613,969 A | 3/1997 | Jenkins, Jr. |
| 5,628,749 A | 5/1997 | Vendrely |
| 5,639,279 A | 6/1997 | Burkinshaw |
| 5,643,272 A | 7/1997 | Haines |
| 5,643,402 A | 7/1997 | Mumme |
| 5,649,928 A | 7/1997 | Grundei |
| 5,653,714 A | 8/1997 | Dietz |
| 5,658,293 A | 8/1997 | Vanlaningham |
| 5,667,511 A | 9/1997 | Vendrely |
| 5,681,354 A | 10/1997 | Eckhoff |
| 5,682,886 A | 11/1997 | Delp |
| 5,690,632 A | 11/1997 | Schwartz |
| 5,690,635 A | 11/1997 | Matsen, III |
| 5,690,637 A | 11/1997 | Wen |
| 5,697,935 A | 12/1997 | Moran |
| 5,702,458 A | 12/1997 | Burstein |
| 5,723,016 A | 3/1998 | Minns |
| 5,725,530 A | 3/1998 | Popken |
| 5,728,162 A | 3/1998 | Eckhoff |
| 5,755,801 A | 5/1998 | Walker |
| 5,755,803 A | 5/1998 | Haines |
| 5,755,804 A | 5/1998 | Schmotzer |
| 5,766,257 A | 6/1998 | Goodman |
| 5,769,855 A | 6/1998 | Bertin |
| 5,769,899 A | 6/1998 | Schwartz |
| 5,776,200 A | 7/1998 | Johnson |
| 5,782,921 A | 7/1998 | Colleran |
| 5,782,925 A | 7/1998 | Collaz |
| 5,799,055 A | 8/1998 | Peshkin |
| 5,800,552 A | 9/1998 | Forte |
| 5,810,827 A | 9/1998 | Haines |
| 5,824,100 A | 10/1998 | Kester |
| 5,824,102 A | 10/1998 | Buscayret |
| 5,824,105 A | 10/1998 | Ries |
| 5,871,545 A | 2/1999 | Goodfellow |
| 5,871,546 A | 2/1999 | Colleran |
| 5,879,354 A | 3/1999 | Haines |
| 5,879,392 A | 3/1999 | McMinn |
| 5,906,643 A | 5/1999 | Walker |
| 5,908,424 A | 6/1999 | Bertin |
| 5,925,049 A | 7/1999 | Gustilo |
| 5,935,173 A | 8/1999 | Roger |
| 5,944,758 A | 8/1999 | Mansat |
| 5,954,770 A | 9/1999 | Schmotzer |
| 5,980,526 A | 11/1999 | Johnson |
| 5,986,169 A | 11/1999 | Gjunter |
| 5,997,577 A | 12/1999 | Herrington |
| 6,039,764 A | 3/2000 | Pottenger |
| 6,056,754 A | 5/2000 | Haines |
| 6,059,788 A | 5/2000 | Katz |
| 6,068,658 A | 5/2000 | Insall |
| 6,080,195 A | 6/2000 | Colleran |
| 6,083,228 A * | 7/2000 | Michelson ............ 606/79 |
| 6,099,570 A | 8/2000 | Livet |
| 6,110,182 A | 8/2000 | Mowlai-Ashtiani |
| 6,120,543 A | 9/2000 | Meesenburg |
| 6,132,468 A | 10/2000 | Mansmann |
| 6,139,581 A | 10/2000 | Engh |
| 6,165,223 A | 12/2000 | Metzger |
| 6,171,340 B1 | 1/2001 | McDowell |
| 6,195,577 B1 | 2/2001 | Truwit |
| 6,197,064 B1 | 3/2001 | Haines |
| 6,203,576 B1 | 3/2001 | Afriat |
| 6,206,926 B1 | 3/2001 | Pappas |
| 6,210,443 B1 | 4/2001 | Marceaux |
| 6,235,060 B1 | 5/2001 | Meesenburg |
| 6,236,875 B1 | 5/2001 | Becholz |
| 6,264,697 B1 | 7/2001 | Walker |
| 6,285,902 B1 | 9/2001 | Kienzle |
| 6,306,146 B1 | 10/2001 | Dinkler |
| 6,306,172 B1 | 10/2001 | O'Neil |
| 6,325,828 B1 | 12/2001 | Dennis |
| 6,340,363 B1 | 1/2002 | Bolger |
| 6,342,075 B1 | 1/2002 | MacArthur |
| 6,348,058 B1 | 2/2002 | Melkent |
| 6,361,564 B1 | 3/2002 | Marceaux |
| 6,368,353 B1 | 4/2002 | Arcand |
| 6,375,658 B1 | 4/2002 | Hangody |
| 6,379,388 B1 | 4/2002 | Ensign |
| 6,401,346 B1 | 6/2002 | Roberts |
| 6,406,497 B2 | 6/2002 | Takei |
| 6,413,279 B1 | 7/2002 | Metzger |
| 6,430,434 B1 | 8/2002 | Mittelstadt |
| 6,436,145 B1 | 8/2002 | Miller |
| 6,443,991 B1 | 9/2002 | Running |
| 6,458,128 B1 | 10/2002 | Schulze |
| 6,470,207 B1 | 10/2002 | Simon |
| 6,475,241 B2 | 11/2002 | Pappas |
| 6,477,400 B1 | 11/2002 | Barrick |
| 6,482,409 B1 | 11/2002 | Lobb |
| 6,485,519 B2 | 11/2002 | Meyers |
| 6,491,699 B1 | 12/2002 | Henderson |
| 6,491,726 B2 | 12/2002 | Pappas |
| 6,500,208 B1 | 12/2002 | Metzger |
| 6,506,215 B1 | 1/2003 | Letot |
| 6,520,964 B2 | 2/2003 | Tallarida |
| 6,554,838 B2 | 4/2003 | McGovern |
| 6,575,980 B1 | 6/2003 | Robie |
| 6,579,290 B1 | 6/2003 | Hardcastle |
| 6,595,997 B2 | 7/2003 | Axelson |
| 6,620,198 B2 | 9/2003 | Burstein |
| 6,623,526 B1 | 9/2003 | Lloyd |
| 6,645,251 B2 | 11/2003 | Salehi |
| 6,679,917 B2 | 1/2004 | Ek |
| 6,685,711 B2 | 2/2004 | Axelson |
| 6,694,168 B2 | 2/2004 | Traxel |
| 6,694,768 B2 | 2/2004 | Lu |
| 6,695,848 B2 | 2/2004 | Haines |
| 6,697,664 B2 | 2/2004 | Kienzle |
| 6,697,768 B2 | 2/2004 | Lue |
| 6,701,174 B1 | 3/2004 | Krause |
| 6,702,821 B2 | 3/2004 | Bonutti |
| 6,711,432 B1 | 3/2004 | Krause |
| 6,725,080 B2 | 4/2004 | Melkent |
| 6,755,563 B2 | 6/2004 | Wahlig |
| 6,755,864 B1 | 6/2004 | Brack |
| 6,672,224 B1 | 7/2004 | Tallarida |
| 6,764,516 B2 | 7/2004 | Pappas |
| 6,770,097 B2 | 8/2004 | Leclercq |
| 6,773,461 B2 | 8/2004 | Meyers |
| 6,783,550 B2 | 8/2004 | MacArthur |
| 6,796,988 B2 | 9/2004 | Melkent |
| 6,827,723 B2 | 12/2004 | Carson |
| 6,858,032 B2 | 2/2005 | Chow |
| 6,875,222 B2 | 4/2005 | Long |
| 6,886,684 B2 | 5/2005 | Hacikyan |
| 6,898,858 B1 | 5/2005 | Spell |
| 6,911,044 B2 | 6/2005 | Fell |
| 6,916,324 B2 | 7/2005 | Sanford |
| 6,916,340 B2 | 7/2005 | Metzger |
| 6,942,627 B2 | 9/2005 | Huitema |
| 6,942,694 B2 | 9/2005 | Liddicoat |
| 7,018,418 B2 | 3/2006 | Amrich |
| 7,029,477 B2 | 4/2006 | Grimm |
| 7,048,741 B2 | 5/2006 | Swanson |
| 7,077,867 B2 | 7/2006 | Pope |
| 7,104,966 B2 | 9/2006 | Shilber |
| 7,104,996 B2 | 9/2006 | Bonutti |
| 7,141,053 B2 | 11/2006 | Rosa |
| 7,172,596 B2 | 2/2007 | Coon |
| 7,175,630 B2 | 2/2007 | Farling |
| 7,241,298 B2 | 7/2007 | Nemec |
| 7,326,252 B2 | 2/2008 | Otto |

| | | |
|---|---|---|
| 7,344,541 B2 | 3/2008 | Haines |
| 7,371,240 B2 | 5/2008 | Pinczewski |
| 7,422,605 B2 | 9/2008 | Burstein |
| 7,491,235 B2 | 2/2009 | Fell |
| 7,922,771 B2 | 4/2011 | Otto |
| 2001/0018615 A1 | 8/2001 | Biegun |
| 2001/0044627 A1 | 11/2001 | Justin |
| 2001/0049558 A1 | 12/2001 | Liddicoat |
| 2002/0029038 A1* | 3/2002 | Haines ............................ 606/54 |
| 2002/0055784 A1 | 5/2002 | Burstein |
| 2002/0103541 A1 | 8/2002 | Meyers |
| 2002/0107576 A1 | 8/2002 | Meyers |
| 2002/0120340 A1 | 8/2002 | Metzger |
| 2002/0161447 A1 | 10/2002 | Salehi |
| 2003/0028196 A1 | 2/2003 | Bonutti |
| 2003/0055501 A1 | 3/2003 | Fell |
| 2003/0055509 A1 | 3/2003 | McCue |
| 2003/0060882 A1 | 3/2003 | Fell |
| 2003/0060883 A1 | 3/2003 | Fell |
| 2003/0060884 A1 | 3/2003 | Fell |
| 2003/0060885 A1 | 3/2003 | Fell |
| 2003/0069585 A1 | 4/2003 | Axelson |
| 2003/0069591 A1 | 4/2003 | Carson |
| 2003/0093156 A1 | 5/2003 | Metzger |
| 2003/0130665 A1 | 7/2003 | Pinczewski |
| 2003/0158606 A1 | 8/2003 | Coon |
| 2003/0181986 A1 | 9/2003 | Buchholz |
| 2003/0208122 A1 | 11/2003 | Melkent |
| 2003/0212413 A1 | 11/2003 | Wilk |
| 2004/0039396 A1 | 2/2004 | Couture |
| 2004/0044414 A1 | 3/2004 | Nowakowski |
| 2004/0122305 A1 | 6/2004 | Grimm |
| 2004/0152970 A1 | 8/2004 | Hunter |
| 2004/0153066 A1 | 8/2004 | Coon |
| 2004/0199249 A1 | 10/2004 | Fell |
| 2004/0199250 A1 | 10/2004 | Fell |
| 2004/0249467 A1 | 12/2004 | Meyers |
| 2004/0249471 A1 | 12/2004 | Bindseil |
| 2004/0267363 A1 | 12/2004 | Fell |
| 2005/0033424 A1 | 2/2005 | Fell |
| 2005/0149038 A1 | 7/2005 | Haines |
| 2005/0149039 A1 | 7/2005 | Haines |
| 2005/0149040 A1 | 7/2005 | Haines |
| 2005/0171604 A1 | 8/2005 | Michalow |
| 2005/0283251 A1 | 12/2005 | Coon |
| 2006/0015115 A1 | 1/2006 | Haines |
| 2006/0015116 A1 | 1/2006 | Haines |
| 2006/0015117 A1 | 1/2006 | Haines |
| 2006/0030853 A1 | 2/2006 | Haines |
| 2006/0030854 A1 | 2/2006 | Haines |
| 2006/0030855 A1 | 2/2006 | Haines |
| 2006/0030944 A1 | 2/2006 | Haines |
| 2006/0052875 A1 | 3/2006 | Bernero |
| 2006/0058882 A1 | 3/2006 | Haines |
| 2007/0078517 A1 | 4/2007 | Engh |
| 2007/0179607 A1 | 8/2007 | Hodorek |
| 2008/0154270 A1 | 6/2008 | Haines |
| 2009/0076514 A1 | 3/2009 | Haines |
| 2009/0082773 A1 | 3/2009 | Haines |
| 2009/0138018 A1 | 5/2009 | Haines |

FOREIGN PATENT DOCUMENTS

| | | |
|---|---|---|
| EP | 0121142 | 10/1984 |
| EP | 0189253 | 7/1986 |
| EP | 0243109 | 10/1987 |
| EP | 0327249 | 8/1989 |
| EP | 0337901 | 10/1989 |
| EP | 0380451 | 1/1990 |
| EP | 0941719 | 9/1990 |
| EP | 0415837 | 3/1991 |
| EP | 0466659 A2 | 1/1992 |
| EP | 0538153 A1 | 4/1993 |
| EP | 0555003 | 8/1993 |
| EP | 556998 | 8/1993 |
| EP | 0682916 A2 | 11/1995 |
| EP | 0761242 | 3/1997 |
| EP | 0916321 | 5/1999 |
| EP | 0923916 | 6/1999 |
| EP | 0970667 | 1/2000 |
| EP | 0988840 | 3/2000 |
| FR | 2635675 | 3/1990 |
| FR | 2664157 A1 | 1/1992 |
| FR | 2701387 | 8/1994 |
| FR | 2710258 | 3/1995 |
| FR | 2760352 | 9/1998 |
| GB | 1409150 | 10/1975 |
| GB | 2007980 | 7/1982 |
| GB | 2296443 | 7/1996 |
| GB | 2324249 | 10/1998 |
| GB | 2335145 | 9/1999 |
| JP | 02-501806 | 1/1983 |
| JP | 58-209343 | 12/1983 |
| JP | 61-170453 | 8/1986 |
| JP | 62-133948 | 6/1987 |
| JP | 62-254750 | 6/1987 |
| JP | 01-119244 | 5/1989 |
| JP | 01-126957 | 5/1989 |
| JP | 01-209055 | 8/1989 |
| JP | 02-057247 | 2/1990 |
| JP | 02-234756 | 9/1990 |
| JP | 02-234757 | 9/1990 |
| JP | 02-243143 | 9/1990 |
| JP | 239861 | 9/1990 |
| JP | 02-246971 | 10/1990 |
| JP | 2002/274214 | 11/1990 |
| JP | 03-032663 | 2/1991 |
| JP | 04-297254 | 10/1992 |
| JP | 04-361746 | 12/1992 |
| JP | 05-003880 | 1/1993 |
| JP | 05-502814 | 5/1993 |
| JP | 5-41510 | 6/1993 |
| JP | 05-269140 | 10/1993 |
| JP | 05-277130 | 10/1993 |
| JP | 06-08033 | 1/1994 |
| JP | 06-38971 | 2/1994 |
| JP | 6-217984 | 8/1994 |
| JP | 06-233775 | 8/1994 |
| JP | 06-237941 | 8/1994 |
| JP | 7-501966 | 3/1995 |
| JP | 7-116185 | 5/1995 |
| JP | 7-136200 | 5/1995 |
| RU | 2121319 | 11/1998 |
| SE | 382155 | 1/1976 |
| SU | 577020 T | 10/1977 |
| WO | WO 81/03122 | 11/1981 |
| WO | WO 91/00061 | 1/1991 |
| WO | WO 91/10408 | 7/1991 |
| WO | WO 93/22990 | 11/1993 |
| WO | WO 93/25157 | 12/1993 |
| WO | WO 94/05212 | 3/1994 |
| WO | WO 94/08528 | 4/1994 |
| WO | WO 94/09730 | 5/1994 |
| WO | WO 94/14366 | 7/1994 |
| WO | WO 94/22397 | 10/1994 |
| WO | WO96/01588 | 1/1996 |
| WO | WO96/07361 A1 | 3/1996 |
| WO | WO 96/24295 | 8/1996 |
| WO | WO 97/05827 | 2/1997 |
| WO | WO97/29703 A1 | 8/1997 |
| WO | WO97/29704 A1 | 8/1997 |
| WO | WO 9820817 | 5/1998 |
| WO | WO 99/27872 | 6/1999 |
| WO | WO 99/30649 | 6/1999 |
| WO | WO 01/13825 | 3/2001 |
| WO | WO02/34310 | 5/2002 |
| WO | WO2004/069036 | 8/2004 |
| WO | WO2004/070580 | 8/2004 |
| WO | WO2004/100758 | 11/2004 |
| WO | WO2004/100839 | 11/2004 |

OTHER PUBLICATIONS

E. Marlowe Goble and Daniel F. Justin, *Minimally invasive total knee replacement: principles and technique*, Orthop. Clin. N. Am. 35 (2004) 235-245.

Whiteside Ortholoc Total Knee System: Surgical Procedure, Dow Corning Wright, pp. WMT000001-WMT000040, Jun. 1985.

Zimmer, Insall/Burstein II, *Constrained Condylar: Modular Knee*

*System*, 35 pages, copyright 1989.
File History for U.S. Appl. No. 12/187,210, filed Aug. 6, 2008.
File History for U.S. Appl. No. 11/075,836, filed Mar. 8, 2005.
File History for U.S. Appl. No. 11/075,836, filed Mar. 8, 2005.
U.S. Appl. No. 12/171,843, Inventor: Haines, Filed Jul. 11, 2008.
U.S. Appl. No. 11/825,857, Inventor: Haines, Filed Jul. 9, 2007.
U.S. Appl. No. 11/036,584, Inventor: Haines, Filed Jan. 14, 2005.
File History for U.S. Appl. No. 11/075,840, filed Mar. 8, 2005.
U.S. Appl. No. 11/075,552, Inventor: Haines, Filed Mar. 8, 2005.
File History for U.S. Appl. No. 11/049,634, filed Feb. 5, 2005.
File History for U.S. Appl. No. 11/074,599, filed Mar. 8, 2005.
File History for U.S. Appl. No. 11/075,553, filed Mar. 8, 2005.
U.S. Appl. No. 12/638,692, filed Dec. 15, 2009, Haines.
Freeman Samuelson, *Total Knee System,* published by Biomet, Inc., 1994 ("Biomet Brochure").
Freeman, Mark II *Total Knee Replacement System,* published 1985.
Protek F/S Modular Total Knee Replacement System, pp. 1-57, published by Protek in Jan. 1991.
*Low Contact Stress Meniscal Bearing Unicompartmental Knee Replacement: Long-Term Evaluation of Cemented and Cementless Results,*Journal of Orthopaedic Rheumatology (presented at the 57$^{th}$ Annual American Academy of Orthopaedic Surgeons Meetings, New Orleans, LA, Feb. 11, 1990), Bates No. DEP00004096-DEP00004107.
N.J. Unicompartmental Knee, Dated Sep. 15, 1989, Bates No. DEP00004108-DEP00004116.
Buechel, Frederick F., *NJ LCS Unicompartmental Knee System with Porocoat,* dated Oct. 24, 1994, Bates No. DEP000004117-DEP00004130.
Buechel, Frederick F. *NJ LCD Unicompartmental Knee System with Porocoat,* 1994, Bates No. DEP00004131-DEP00004141.
Buechel, Frederick F. *NJ LCS Unicompartmental Knee System with Porocoat,* 1994, Bates No. DEP00004142-DEP00004152.
Engh, et al., *The AMK Total Knee System, Design Rationale and Surgical Procedure,* dated 1989, Bates No. DEP00004153-DEP00004201.
*Advertising Proteck Mark II PCR Total Knee Replacement System,* Journal of Bone and Joint Surgery, 1987, Bates No. DEP00004202-DEP00004230.
Protek, *Parts Brochure for Mark II Protek,*1987, Bates No. DEP00004231-DEP00004235.
Chapman, Michael W., *Operative Orthopaedics,* vol. 1, Published by J.B. Lipponcott Co., Philadelphia, dated 1988, Bates No. DEP00004236- DEP00004247.
American Academy of Orthopaedic Surgeons, *Flyer from 57$^{th}$ Annual American Academy of Orthopaedic Surgeons Meeting,*Feb. 13, 1990, Bates No. DEP00004248-DEP00004251.
Crossett et al., *AMK Congruency Instrument System, Surgical Technique,* dated 1997, Bates No. DEP00004252-DEP00004267.
Engh et al., *AMK Surgical Technique,* Bates No. DEP00004268-DEP00004298, dated 1989.
Engh et al., *AMK Surgical Technique,* Bates No. DEP00004299-DEP0004329, dated 1989.
Crenshaw, A.H., *Campbell's Operative Orthopaedics,* 4$^{th}$ Edition, vol. 1, Bates No. DEP00004330-DEP00004333, dated 1963.
Howmedica, *Duraconcept, Design Concepts of the Duracon Total Knee System,* Bates No. DEP00004337-DEP00004337, dated 1993.
Freeman et al., *Total Knee System,*Bates No. DEP00004350-DEP00004361, Published prior to Jun. 7, 1994.
freeman et al., *F/S Modular Total Knee Replacement System-SICOT,* 90 Edition, Bates No. DEP00004362-DEP00004373, dated 1990.
Buechel, Frederick F., *Howmedica Product Catalog,* Bates No. Dep 00004374-DEP00004375, dated 1994.
Massarella, Antony, *Interax Bulletin, No. 6, Tibial Intramedullary Alignment Surgical Technique,* Bates No. DEP00004387-DEP0000-4390, dated Feb. 23, 1994.
Desjardins et al., *Interax Operative Technique,* Bates No. DEP00004391-DEP00004411, dated 1994.
Desjardins et al., *Interax Total Knee Operative Technique: Monogram Total Knee Instruments,* Bates No. DEP00004412-DEP00004432, dated 1993.
Howmedica, *Interax Tibial IM,*Bates No. DEP00004433-DEP00004434, dated 1994.
Depuy, *LCS Uni PMA Data from FDA Website,*Bates No. DEP00004434- DEP00004434, dated 1991.
Briard et al., *LCS Uni Unicompartmental Knee System with Porocoat,*Bates No. DEP00004452-DEP00004462, dated 1991.
Freeman et al., *Mark II Total Knee Replacement System,*Bates No. DEP00004463-DEP00004492, dated 1985.
Buechel, Frederick F., *NJ LCS Unicompartmental Knee System with Porocoat,*Bates No. DEP00004493-DEP00004503, dated 1994.
Chapman, Michael W. *Operative Orthopaedics,*vol. 3, 2$^{nd}$ Edition, Published by J.B. Lipponcott Co., BATES No. DEP00004504-DEP00004508, dated 1993.
Biomet, *Oxford Meniscal Knee Phase II Unicompartmental Replacement,*Bates No. DEP00004509-DEP00004515, Published prior to Jun. 7, 1994.
Scott et al., *P.F.C. Sigma Unicompartmental Knee System,*Bates No. DEP00004531-DEP00004539, dated 1998.
Freeman et al., *F/S Modular Total Knee Replacement System,*Bates No. DEP00004540-DEP00004596, dated 1990.
Broughton et al., *Unicompartmental Replacement and High Tibial Osteotomy for Osteoarthritis of the Knee,*Journal of Bone and Joint Surgery, vol. 68-B, No. 3, May 1, 1986, pp. 447-452, Bates No. DEP00004752- DEP00004763.
Scott et al., *Unicompartmental and High Tibial Osteotomy for Osteoarthritis of the Knee,*Journal of Bone and Joint Surgery, vol. 63-A, No. 4, Apr. 1, 1981, Bates No. DEP00004764-DEP00004775.
Thornhill, Thomas S., *Unicompartmental Knee Arthroplasty Clinical Orthopaedics and Related Research,*No. 205, Apr. 1, 1986, pp. 121-131, Bates No. DEP00004776-DEP00004791.
Forst et al., *A Special jg for Tibial Resection for the Implantation of GSB-Knee-Prostheses in Problematic cases,*pp. 162-166, dated Jun. 1, 1984, Bates No. DEP00004838-DEP00004842.
Ingillis et al., *Revision Total Knee Replacement Techniques in Orthopedics,*dated Apr. 1, 1990, Bates No. DEP00005583-DEP00005592.
Uvehammer et al., "In Vivo Kinematics of Total Knee Arthroplasty: Concave Versus Posterior-Stabilised Tibial Joint Surface", vol. 82-B, No. 4, May 2000, pp. 499-505.

* cited by examiner

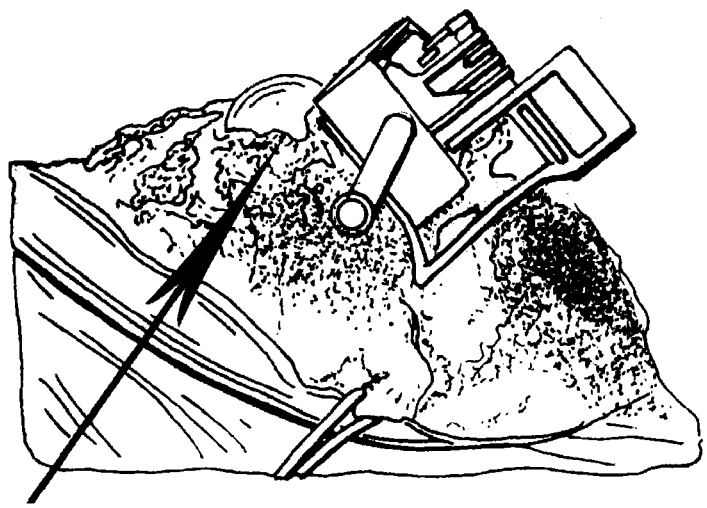
FEMUR *Fig.3A*
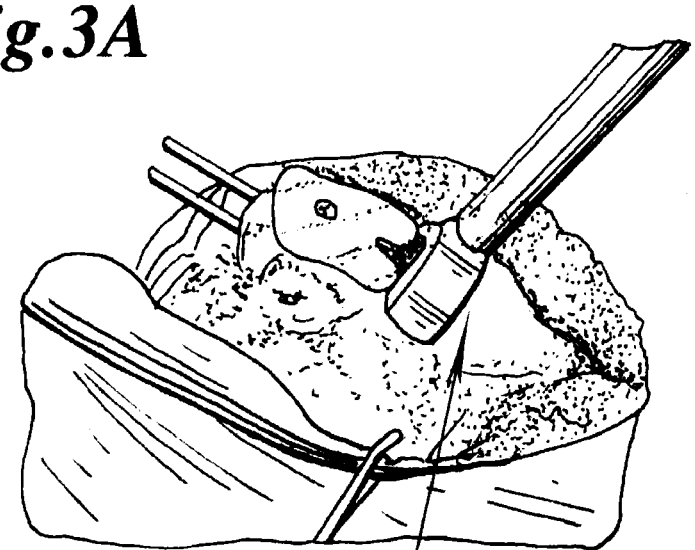
*Fig.3B* TIBIA
PATELLA
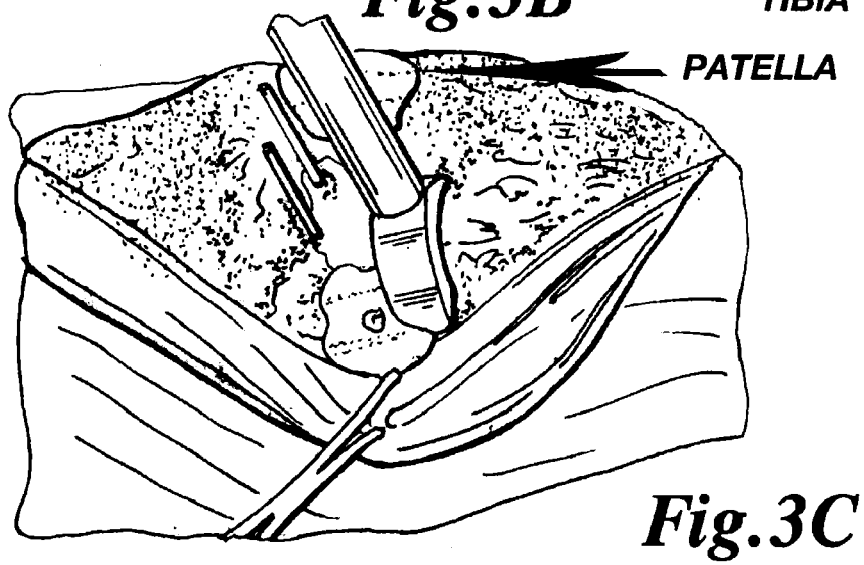
*Fig.3C*

SOFT TISSUE OR PATELLOFEMORAL ACCOMODATING CONTOUR
DRILL GUIDE TINES

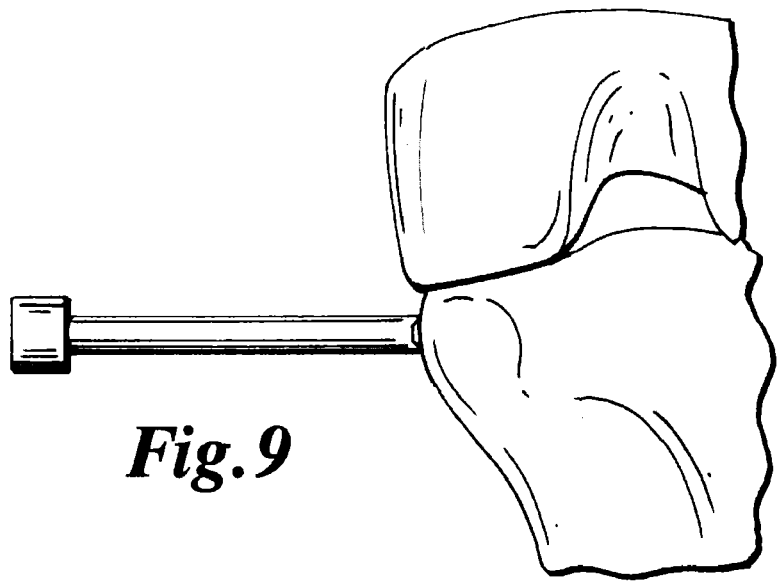
*Fig.9*
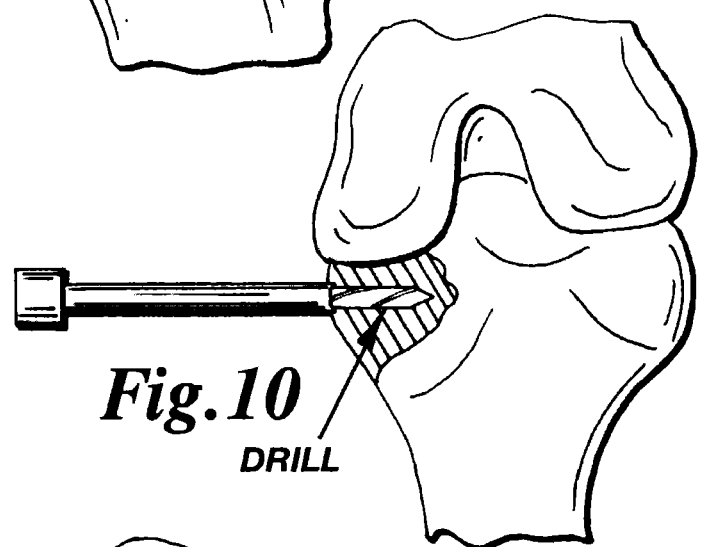
*Fig.10*
DRILL
*Fig.11*

CUTTING GUIDE PATH

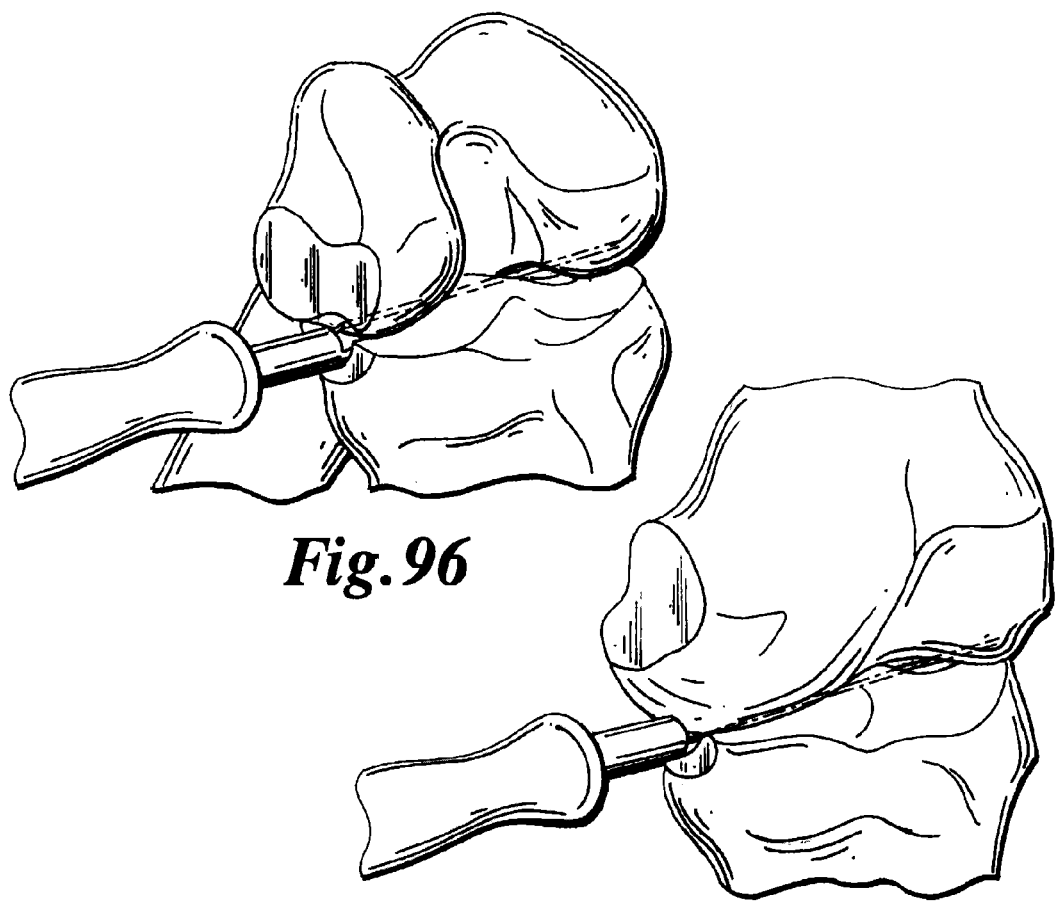
*Fig. 96*
*Fig. 97*
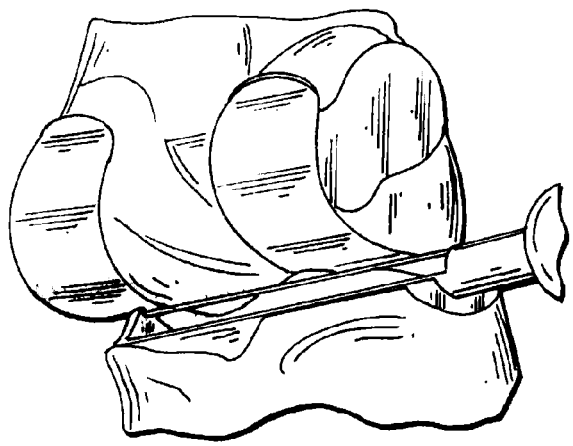
*Fig. 98*

ANTERIOR CUT DRILL HOLES
ANTERIOR CHAMFER CUT DRILL HOLES
POSTERIOR CHAMFER CUT DRILL HOLES
POSTERIOR CUT DRILL HOLES

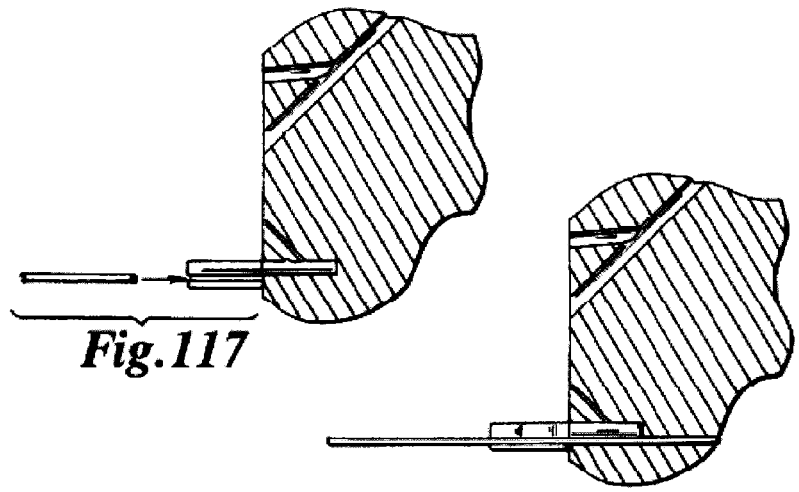
Fig.117
Fig.118
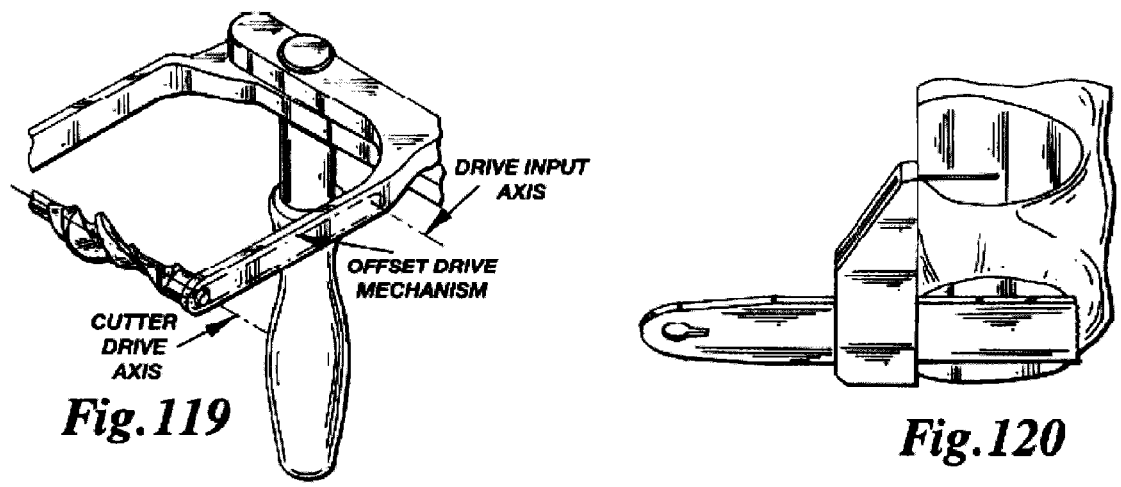
Fig.119
Fig.120

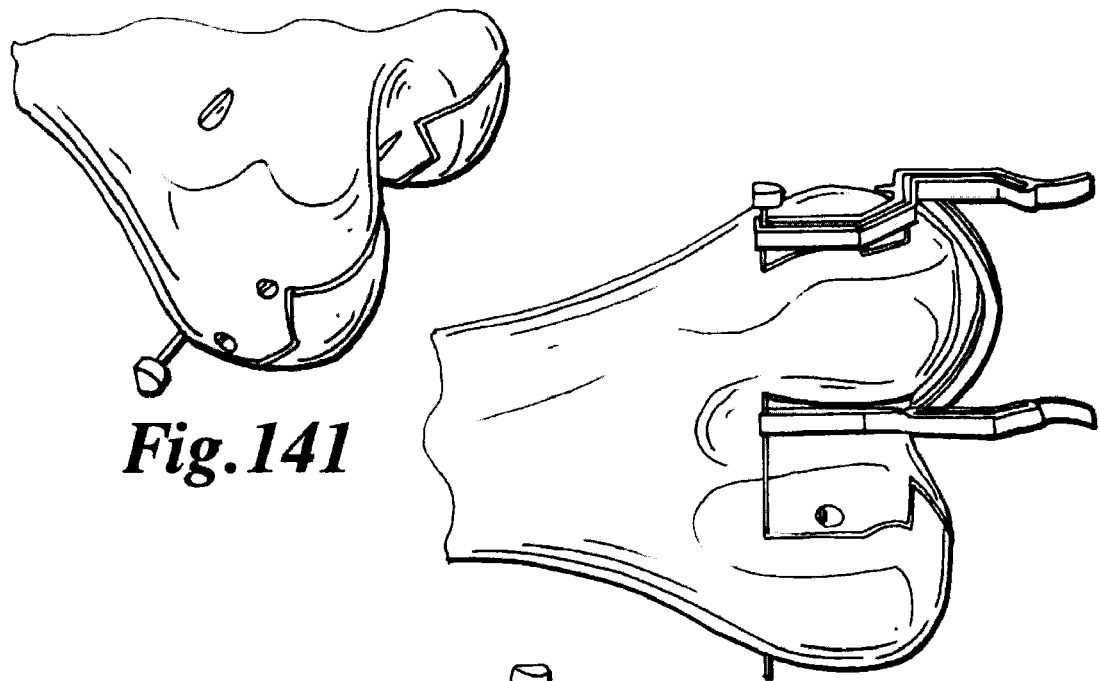
Fig.141
Fig.142
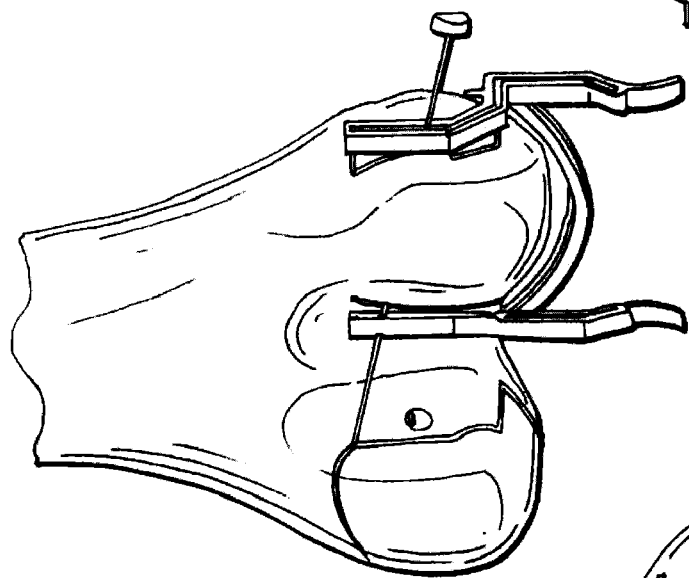
Fig.143
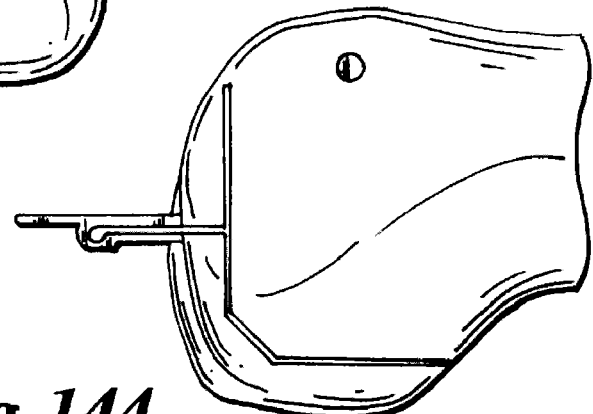
Fig.144

OUTER CUTTING RADIUS
INNER CUTTING RADIUS
CUTTING TEETH

METHODS AND APPARATUS FOR IMPROVED CUTTING TOOLS FOR RESECTION

CLAIM TO PRIORITY

The present invention claims priority to U.S. Provisional Application No. 60/551,307, filed Mar. 8, 2004, entitled, "METHODS AND APPARATUS FOR IMPROVED CUTTING TOOLS FOR RESECTION," and claims priority to U.S. Provisional Application No. 60/551,080, filed Mar. 8, 2004, entitled, "METHODS AND APPARATUS FOR PIVOTABLE GUIDE SURFACES FOR ARTHROPLASTY," and claims priority to U.S. Provisional Application No. 60/551,078, filed Mar. 8, 2004, entitled, "METHODS AND APPARATUS FOR MINIMALLY INVASIVE RESECTION," and claims priority to U.S. Provisional Application No. 60/551,096, filed Mar. 8, 2004, entitled, "METHODS AND APPARATUS FOR ENHANCED RETENTION OF PROSTHETIC IMPLANTS," and claims priority to U.S. Provisional Application No. 60/551,631, filed Mar. 8, 2004, entitled, "METHODS AND APPARATUS FOR CONFORMABLE PROSTHETIC IMPLANTS," and claims priority to U.S. Provisional Application No. 60/551,262, filed Mar. 8, 2004, entitled, "METHODS AND APPARATUS FOR IMPROVED DRILLING AND MILLING TOOLS FOR RESECTION," and claims priority to U.S. Provisional Application No. 60/551,160, filed Mar. 8, 2004, entitled, "METHODS AND APPARATUS FOR IMPROVED PROFILE BASED RESECTION," and is a continuation-in-part of U.S. patent application Ser. No. 11/036,584, filed Jan. 14, 2005, entitled, "METHODS AND APPARATUS FOR PINPLASTY BONE RESECTION," which claims priority to U.S. Provisional Application No. 60/536,320, filed Jan. 14, 2004, and is a continuation-in-part of U.S. patent application Ser. No. 11/049,634, filed Feb. 2, 2005 now abandoned, entitled, "METHODS AND APPARATUS FOR WIREPLASTY BONE RESECTION," which claims priority to U.S Provisional Application No. 60/540,992, filed Feb. 2, 2004, entitled, "METHODS AND APPARATUS FOR WIREPLASTY BONE RESECTION," the entire disclosures of which are hereby fully incorporated by reference.

BACKGROUND OF THE INVENTION

1. Field of the Invention

This invention generally relates to methods and apparatus for bone resection to allow for the interconnection or attachment of various prosthetic devices with respect to the patient. More particularly, the present invention relates to methods and apparatus for improved cutting tools for resection and arthroplasty.

2. Background Art

Different methods and apparatus have been developed in the past to enable a surgeon to remove bony material to create specifically shaped surfaces in or on a bone for various reasons including to allow for attachment of various devices or objects to the bone. Keeping in mind that the ultimate goal of any surgical procedure is to restore the body to normal function, it is critical that the quality and orientation of the cut, as well as the quality of fixation, and the location and orientation of objects or devices attached to the bone, is sufficient to ensure proper healing of the body, as well as appropriate mechanical function of the musculoskeletal structure.

In total knee replacements, for example, a series of planar and/or curvilinear surfaces, or "resections," are created to allow for the attachment of prosthetic or other devices to the femur, tibia and/or patella. In the case of the femur, it is common to use the central axis of the femur, the posterior and distal femoral condyles, and/or the anterior distal femoral cortex as guides to determine the location and orientation of distal femoral resections. The location and orientation of these resections are critical in that they dictate the final location and orientation of the distal femoral implant. It is commonly thought that the location and orientation of the distal femoral implant are critical factors in the success or failure of the artificial knee joint. Additionally, with any surgical procedure, time is critical, and methods and apparatus that can save operating room time, are valuable. Past efforts have not been successful in consistently and/or properly locating and orienting distal femoral resections in a quick and efficient manner.

The use of oscillating sawblade based resection systems has been the standard in total knee replacement and other forms of bone resection for over 30 years. Other forms of arcuate and curvilinear sawblades and chisels have been proposed in the past as shown, for example, in U.S. Pat. Nos. 4,069,824 and 4,349,058 and PCT Publ. Appl. WO 97/05827, but these non-planar sawblade arrangement have not been widely accepted or adopted. Unfortunately, present approaches to using existing planar or non-planar saw blade instrumentation systems all possess certain limitations and liabilities.

Perhaps the most critical factor in the clinical success of any bone resection for the purpose of creating an implant surface on the bone is the accuracy of the implant's placement. This can be described by the degrees of freedom associated with each implant. In the case of a total knee arthroplasty (TKA), for example, for the femoral component these include location and orientation that may be described as Varus-Valgus Alignment, Rotational Alignment, Flexion-Extension Alignment, A-P location, Distal Resection Depth Location, and Mediolateral Location. Conventional instrumentation very often relies on the placement of ⅛ or 3/16 inch diameter pin or drill placement in the anterior or distal faces of the femur for placement of cutting guides. In the case of posterior referencing systems for TKA, the distal resection cutting guide is positioned by drilling two long drill bits into the anterior cortex across the longitudinal axis of the bone. As these long drills contact the oblique surface of the femur they very often deflect, following the path of least resistance into the bone. As the alignment guides are disconnected from these cutting guides, the drill pins will "spring" to whatever position was dictated by their deflected course thus changing their designated, desired alignment to something less predictable and/or desirable. This kind of error is further compounded by the "tolerance stacking" inherent in the use of multiple alignment guides and cutting guides.

Another error inherent in these systems further adding to mal-alignment is deflection of the oscillating sawblade during the cutting process. The use of an oscillating sawblade is very skill intensive as the blade will also follow the path of least resistance through the bone and deflect in a manner creating variations in the cut surfaces which further contribute to prosthesis mal-alignment as well as poor fit between the prosthesis and the resection surfaces. Despite the fact that the oscillating saw has been used in TKA and other bone resection procedures for more than 30 years, there are still reports of incidences where poor cuts result in significant gaps in the fit between the implant and the bone.

Improvements in the alignment and operation of cutting tools for resecting bone surfaces are desired in order to increase the consistency and repeatability of bone resection procedures as is the improvement of prosthetic stability in attachment to bone.

SUMMARY OF THE INVENTION

The present invention provides for embodiments of cutting tools and soft tissue management techniques facilitating intraoperative and postoperative efficacy and ease of use. In one embodiment, the cutting tool is a side cutting tool that has only a portion of the arc of the cutting profile exposed for cutting and is preferably used in a dynamic cutting mode where the leg is moved in flexion to engage the exposed portion of the cutting profile. In another embodiment, a cutting tool having dual planar cutting profile, preferably orthogonal to each other, permits the cutting tool to be utilized to create multiple resected surfaces at different orientations without the need to disengage the cutting tool from the guide surfaces. In still another embodiment, the cutting tool is provided with an arcuate cutting blade that preferably engages a guide tool with spaced apart guide surfaces that permit the creation of resected surfaces on both the femor and the tibia for a given condyle without the need to reposition the guide or the leg.

The present invention utilizes a number of embodiments of cutting tools to remove bony material to create cut surfaces for prosthetic implant attachment and fixation. The overriding objects of the embodiments are to provide the ability to perform resection in very small incisions, the creation of precise and accurate cut(s), and to provide for soft tissue protection characteristics and features preventing the tool from accidentally harming soft tissue. Specifically, many of the cutting tool embodiments disclosed are either incapable or highly resistant to damaging soft tissue, or are by means disclosed prevented from coming into contact with soft tissue in the first place.

The present invention utilizes a number of embodiments of cutting guide technologies loosely or directly based on Profile Based Resection (PBR). The overriding objects of PBR technologies are to provide for significantly improved reproducibility of implant fit and alignment in a manner largely independent of the individual surgeon's manual skills, while providing for outstanding ease of use, economic, safety, and work flow performance.

The present invention utilizes a number of embodiments of alignment or drill guides to precisely and accurately determine the desired cutting guide location/orientation, thus cut surface location(s)/orientation(s), thus prosthetic implant location and orientation. The overriding objects of the embodiments are to precisely and accurately dictate the aforementioned locations and orientations while optionally enabling ease of use in conjunction with manually or Computer Assisted techniques, and while optionally enabling ease of use in minimally invasive procedures where surgical exposure and trauma are minimized.

The present invention utilizes a number of methods and apparatus embodiments of soft tissue management techniques and the devices supporting said techniques. The overriding object of these embodiments is to take advantage of the anatomy, physiology, and kinematics of the human body in facilitating clinical efficacy of orthopedic procedures.

It is an often repeated rule of thumb for orthopedic surgeons that a "Well placed, but poorly designed implant will perform well clinically, while a poorly placed, well designed implant will perform poorly clinically." The present invention provides a method and apparatus for reducing implant placement errors in order to create more reproducible, consistently excellent clinical results in a manner that decreases risk to soft tissue, incision or exposure size requirements, manual skill requirements, and/or visualization of cutting action.

It should be clear that applications of the present invention is not limited to Total Knee Arthroplasty or the other specific applications cited herein, but are rather universally applicable to any form of surgical intervention where the resection of bone is required. These possible applications include, but are not limited to Unicondylar Knee Replacement, Hip Arthroplasty, Ankle Arthroplasty, Spinal Fusion, Osteotomy Procedures (such as High Tibial Osteotomy), ACL or PCL reconstruction, and many others. In essence, any application where an expense, accuracy, precision, soft tissue protection or preservation, minimal incision size or exposure are required or desired for a bone resection and/or prosthetic implantation is a potential application for this technology. In addition, many of the embodiments shown have unique applicability to minimally invasive surgical (MIS) procedures and/or for use in conjunction with Surgical Navigation, Image Guided Surgery, or Computer Aided Surgery systems.

BRIEF DESCRIPTION OF THE DRAWINGS

Other important objects and features of the invention will be apparent from the following detailed description of the invention taken in connection with the accompanying drawings in which:

FIGS. 1, 2, and 3 are pictorial representations standard incision sizes or exposure required by the prior art, while

FIGS. 5-11, 29-31, 45-49, 58, 88-98, 104-130, 131-146, 154-168, and 171-176 show various depictions of embodiments and methods in accordance with alternate embodiments of the present invention.

DETAILED DESCRIPTION OF THE PREFERRED EMBODIMENTS

It should be noted that, in many of the figures, the cut surface created by the cutting tool in accordance with the techniques of the present invention are shown as having already been completed for the sake of clarity. Similarly, the bones may be shown as being transparent or translucent for the sake of clarity. The guides/pins, cutting tool, bones, and other items disclosed are may be similarly represented for the sake of clarity or brevity FIGS. 1 through 4

Figure 1:
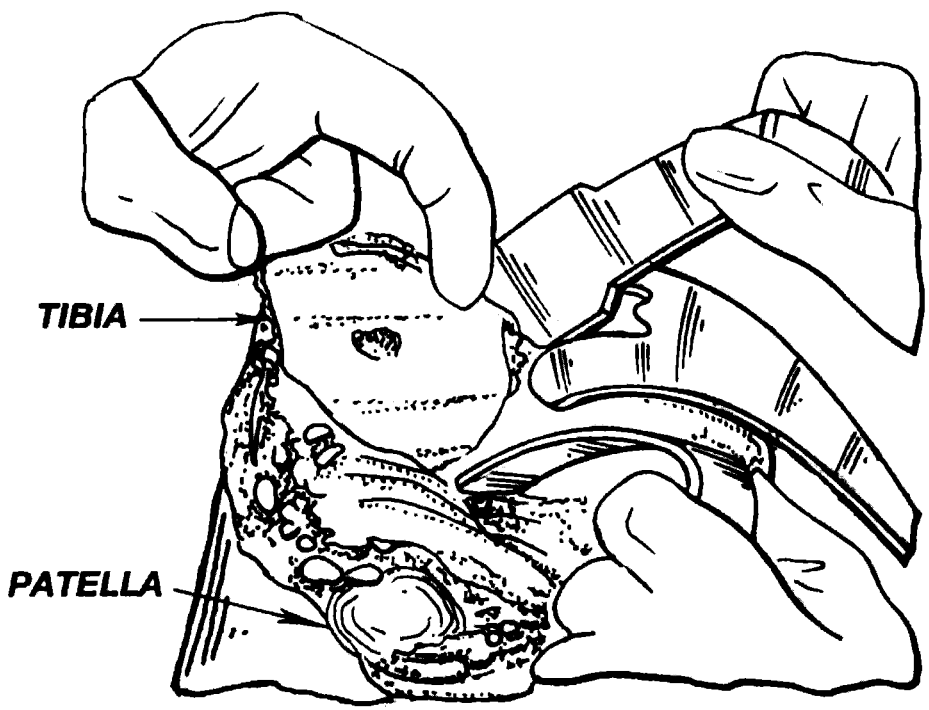
Figure 2:
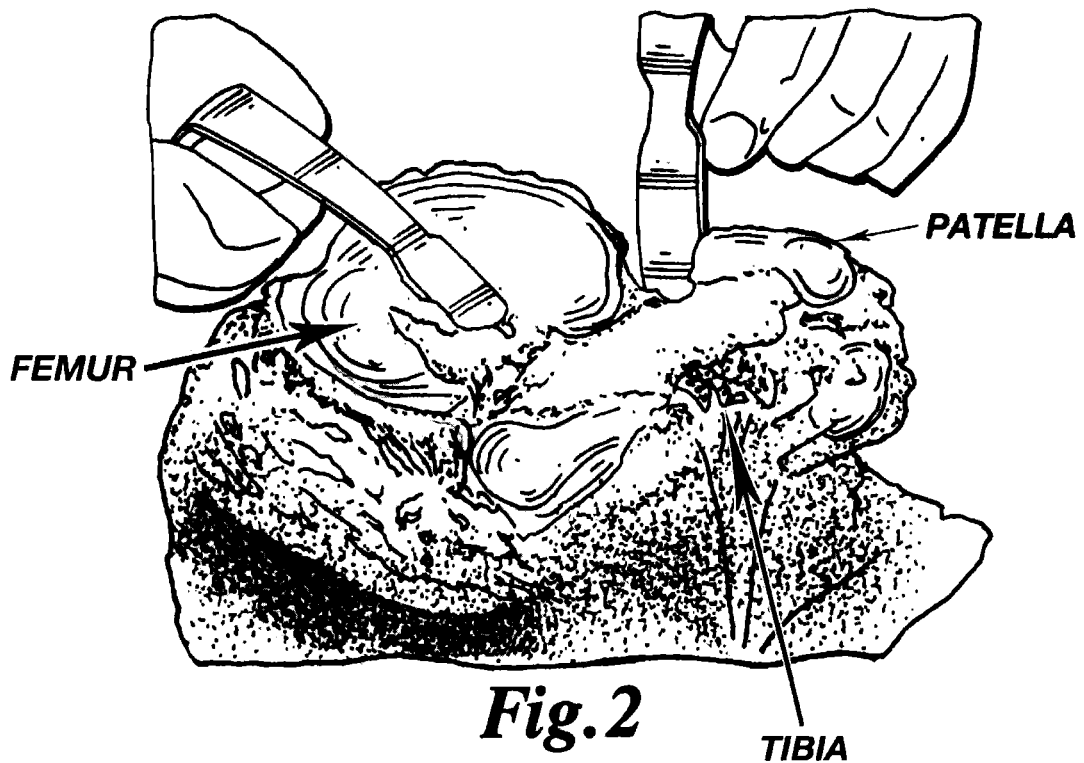
Figure 4:
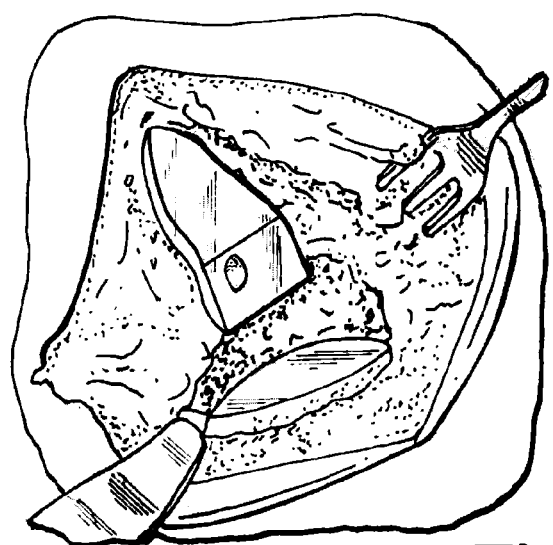
FIG. 4 is a pictorial representation or approximation of one form of surgical exposure that is desired.

FIGS. 1 and 2 show conventional surgical exposures and instrumentation being utilized. FIG. 4 shows a reduced incision currently utilized in performing the current state of the art in 'minimally invasive' Unicondylar Knee Replacement.

FIGS. 29-30 and 93-98

Figure 29:
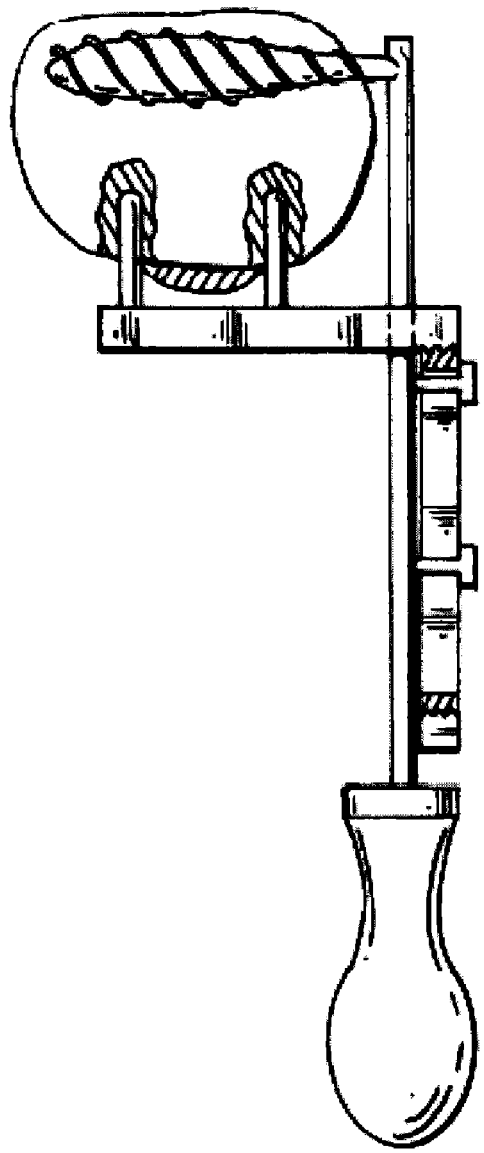
Figure 30:
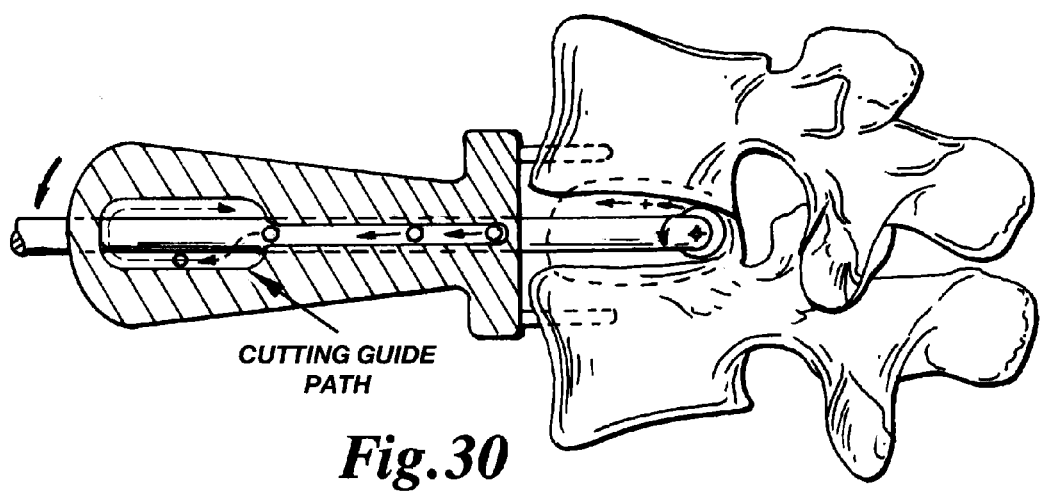
Figure 31:
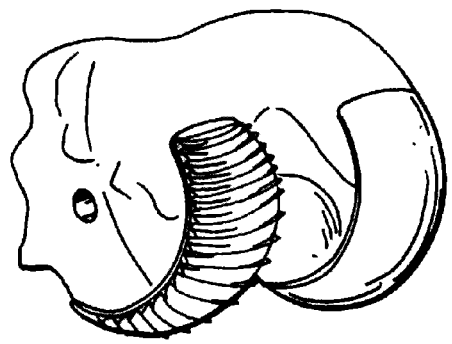
Figure 45:
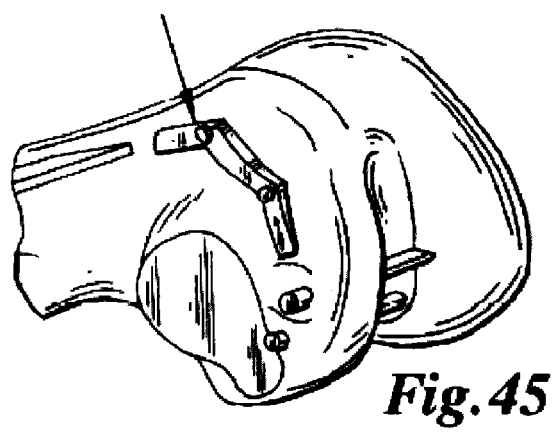
Figure 46:
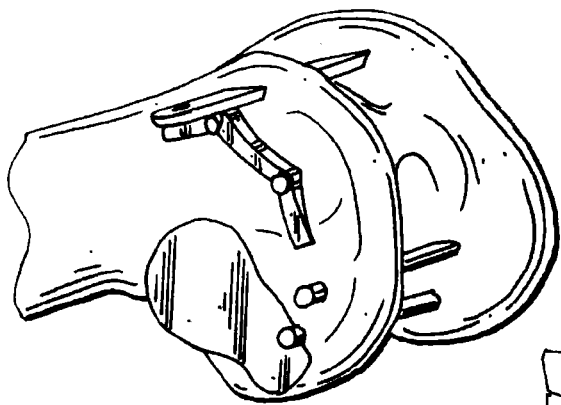
Figure 47:
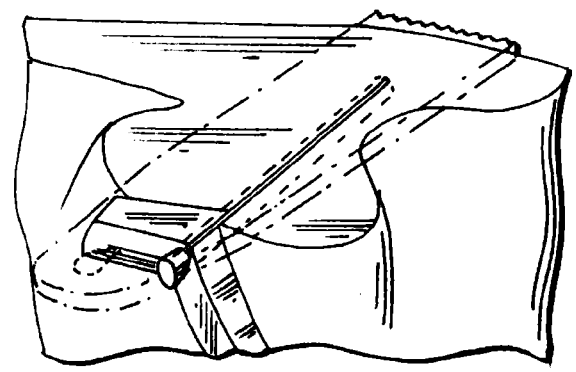
Figure 48:
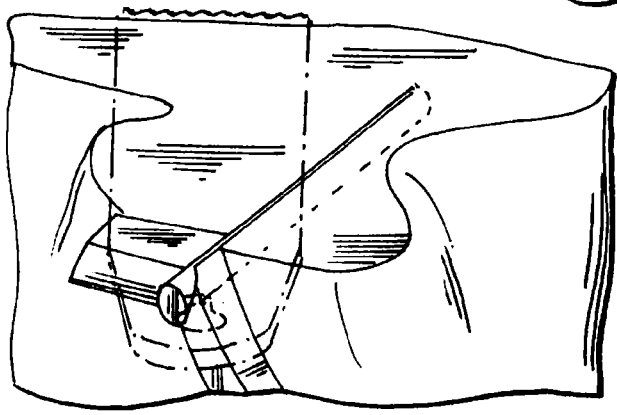
Figure 49:
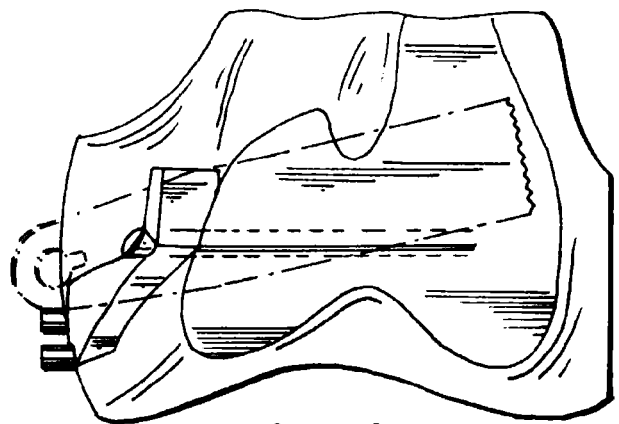

The embodiments of the present invention are shown for femoral resection. For the sake of clarity, it should be noted that any combination of the forms of the present invention disclosed herein may be modified or combined to form constructs not specifically disclosed herein, but still within the scope of the present invention. The embodiments represented in FIGS. 29 and 30 are outstanding examples of this, as one of ordinary skill in the art would clearly recognize the applicability and benefits of this embodiment for tibial and/or femoral resection in Unicondylar or Bicondylar procedures, for bone resection in ankle replacement or arthrodesis (fusion), mandibular advancement procedures, high tibial osteotomy procedures, proximal femoral and acetabular preparation in Hip Arthroplasty, and a list of other applications too long to list in detail where reproducible and safe removal of living tissue during surgical intervention is beneficial.

Figure 94:
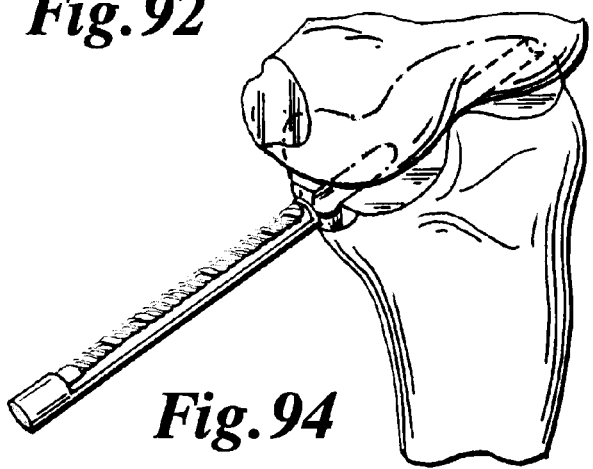
Figure 95:
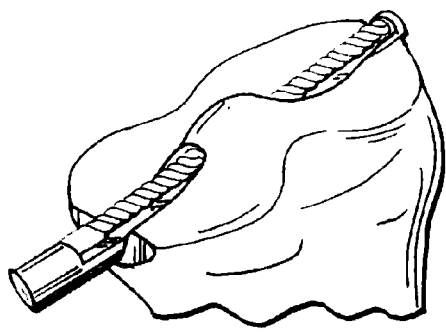

FIGS. 93 through 98 represent an implementation of the side cutting drill embodiment of the present invention for cutting tools. It is of interest to note that the milling handle shown could further be guided by the PBR guides of the present invention to further combine the accuracy and precision benefits of PBR with the soft tissue protection characteristics of tibially embedded femoral cutting tool. It should also be noted that the side cutting drill with a curved cutting profile, similar to that shown in FIG. 119, could also be used to attain cut geometries possessing simultaneously curved or curvilinear cutting profiles and cutting paths. In utilizing such, it would be critical that the side to side location of the cutting profile of the cutting tool be tightly controlled with respect to the desired side to side location of the implant as the side to side location of the implant would be dictated by the cut surfaces generated. Alternatively, a cutting tool with a linear cutting profile, as shown in FIG. 94, could be utilized to create cut surfaces with a linear cutting profile and a curved cutting path, and then a second cutter with a curved cutting profile could be used to create a second, contiguous or non-contiguous, cut with a curved cutting profile and/or path whose mediolateral location was closely controlled to result in proper fit and location of the prosthesis attached to said cut surfaces. It should be noted that the cutting path of the second cutter could be located within a single plane, such as for a bilateral femoral component design, or could be curvilinearly divergent from the plane containing the cutting path of the first cut surface. This would be useful for unilateral femoral component designs (ones which require separate left and right femoral implants) so as to allow for the implant design to reflect out of plane patellofemoral kinematics and/or out of plane tibiofemoral kinematics most accurately. Interestingly, this embodiment of kinematic resection style resection could be modified to allow the cutting tool to be directly or indirectly linked to the movement of the patella with respect to the femur, or directly connected to the patella, to enable cutting of patellofemoral articular surfaces on the femur while moving the tibia and patella through ranges of motion about the tibia. The embodiments of cutting tools for use in attaining this include curvilinear end cutting mills or face cutters, side cutting drills with linear or non-linear cutting profiles, and other cutting tools capable of cutting the femur while engaged, directly or indirectly, to the patella. The side-to-side location of such cutters could be determined by engagement or adjustment with respect to a PBR or other guide, or simply by the natural kinematic path of the patella about the femur during flexion-extension of the knee joint.

FIGS. 130 through 146

Figure 130:
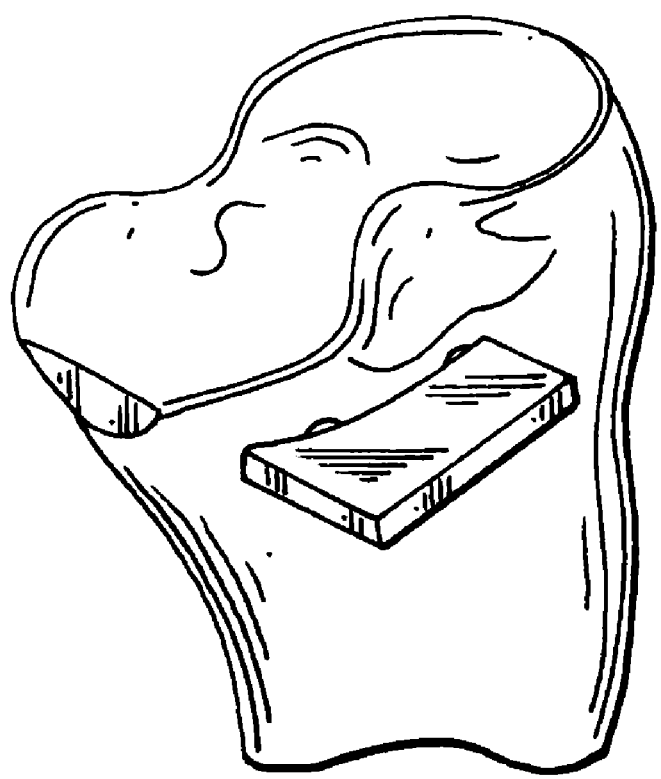

FIG. 130 represents a distal femur with the cuts shown for fixation to a conventional total condylar implant with the border of said cuts shown in black. FIGS. 131 through 146 show embodiments of the present invention for cutting the distal and posterior areas of the femur.

Figure 131:
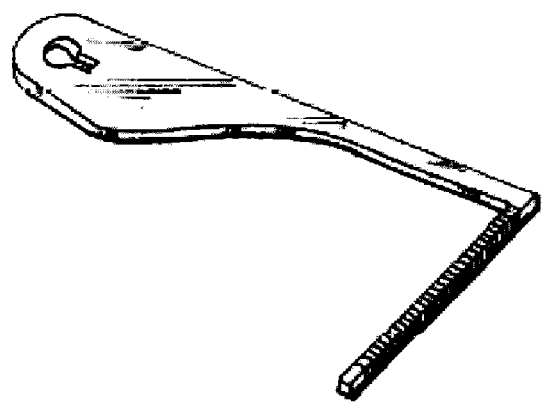
Figure 132:
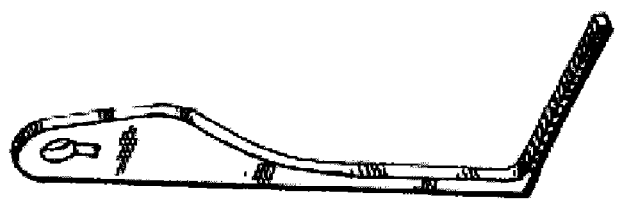
Figure 133:
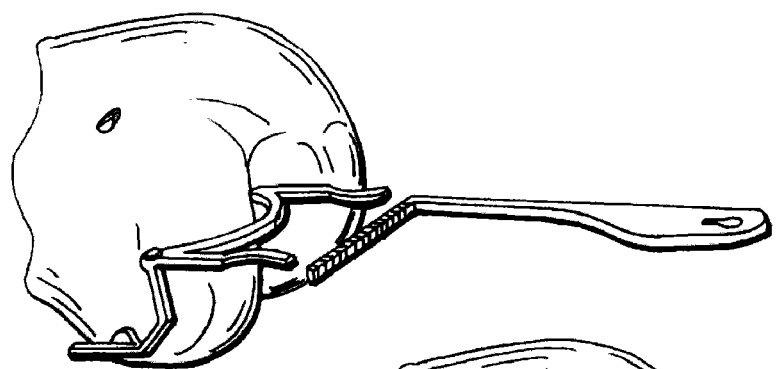
Figure 134:
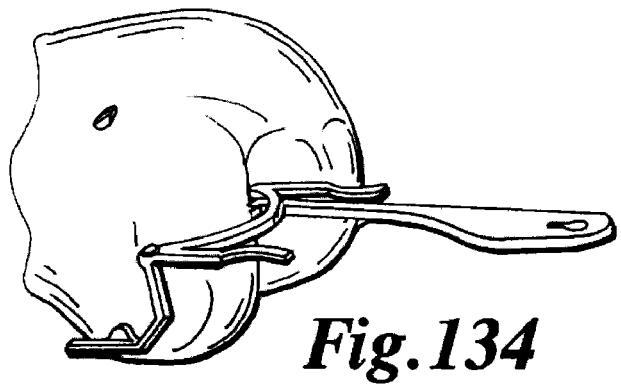
Figure 135:
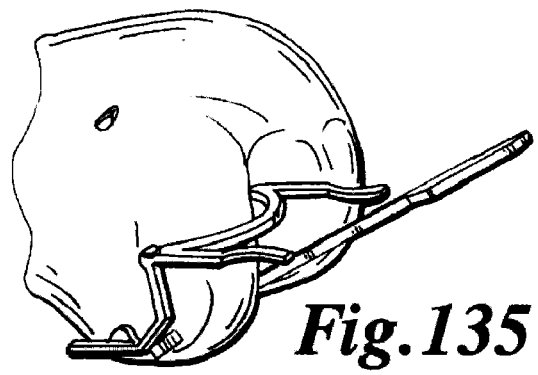

FIG. 131 shows an embodiment of the present invention constituting an improved oscillating saw design. As shown, this design possesses cutting teeth not only on the leading edge as is commonly known in the art, but also on an adjacent surface allowing the saw to cut both while plunging in a direction parallel its long axis and normal to its long axis. FIGS. 132 through 134 show this in use with a cutting guide in cutting the femur. It should be noted that the two smoother areas surrounding the cutting teeth of the saw are intended for bearing contact with a guide, but that bushings, or bearings could be added to facilitate ease of use and avoidance of debris generation.

Figure 136:
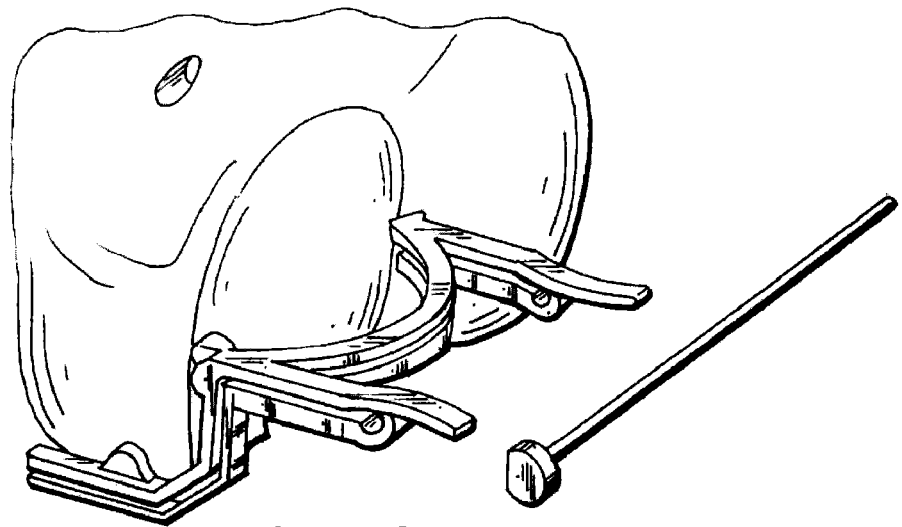
Figure 137:
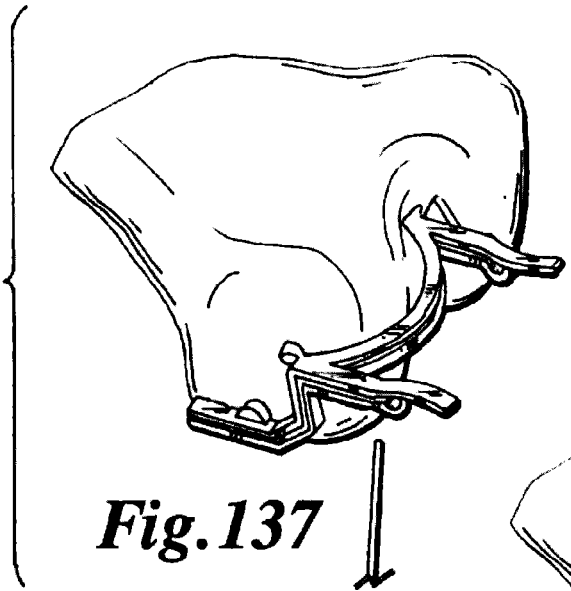
Figure 138:
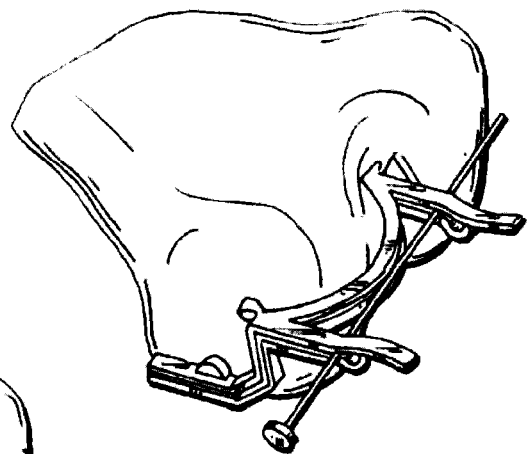
Figure 139:
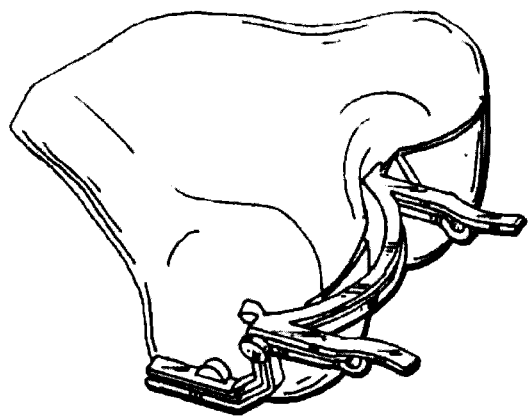
Figure 140:
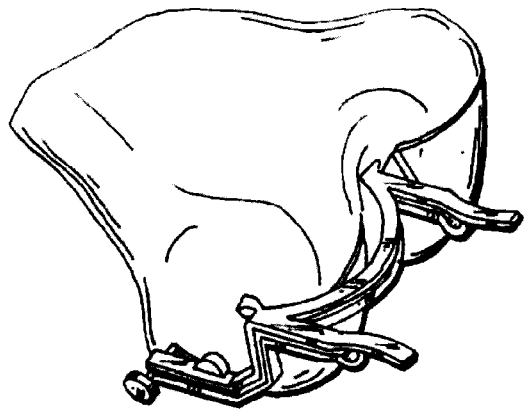
Figure 145:
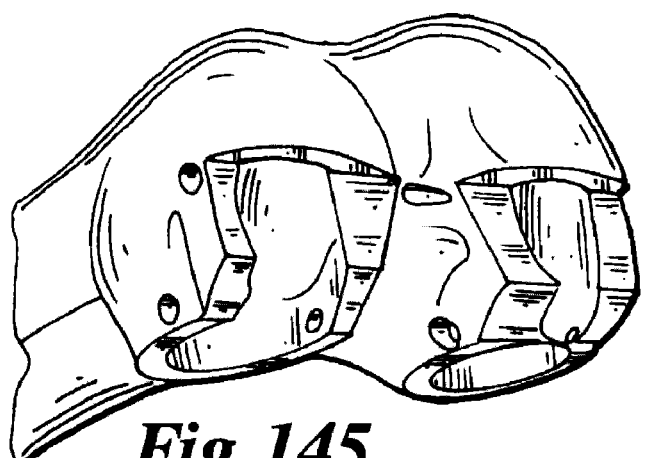
Figure 146:
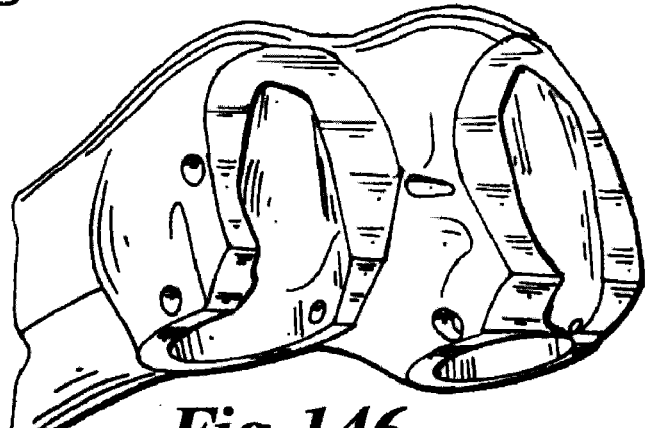

FIGS. 136 through 146 show an alternative cutting means. The small cutting tool best shown in FIG. 136 is a small diameter (0.188 inches to 0.040 inches) side cutting drill, optionally for use in conjunction with a milling handle (not shown). As shown in these figures, a robustly guided cutting tool can be used to cut both condyles when guided by a guide either straddling only one condyle (as shown), or fixed to the medial side of the lateral condyle and the lateral side of the medial condyle. These embodiments may also be applied to cutting of only one condyle, and the cutting path of the guide shown modified to allow for standard or improved Unicondylar use. Also shown, the manipulation of the cutting tool while guided by a PBR guide can include plunging, sweeping and pivotally sweeping manipulations in completing the desired cuts. Once these cuts have been completed, or partially completed and finished by other means, as shown in FIGS. 145 and 146, alternate methods may be employed to complete the remaining cuts. It should be noted that methods allowing for the resection of the posterior femoral condyles and/or the distal femoral condyles in conjunction with the proximal tibia already having been cut, provide for a phenomenal amount of laxity of the soft tissues surrounding the joint allowing for a surgeon to more easily complete cutting of the anterior cut and anterior chamfer cut.

Looking at FIG. 132, it is of special interest to note that the cutting guide surfaces may be attached to a pliers like or milling handle like positioning device which is either guided manually or by a surgical navigation system to determine the ideal location of the rails with respect to the bone. Once the rails were properly positioned, the positioning device could be actuated to cause fixation features (perhaps small spikes, or a serrated or roughened surface capable gripping the bone to which it is in contact with) to grip the bone thus robustly fixing the guide in place. It is also of interest to note that this method and apparatus may be used to position the rails along the sides of a single condyle (as generally shown in FIG. 142), and/or between the condyles (where the gripping surfaces would expand mediolaterally to contact the lateral surface of the medial condyle and the medial surface of the lateral condyle), and/or to the medial side of the medial condyle and the medial side of the lateral condyle (and fixed in place using additional fixation features), and/or about the medial side of the medial condyle and the lateral side of the lateral condyle. In those applications where the rails of the embodiments of the present invention were to be located under soft tissues such as the extensor mechanism, the gripping handle would benefit from the addition of the soft tissue accommodating contours disclosed in the copending provisional patent applications.

FIGS. 154 through 168

Figure 154:
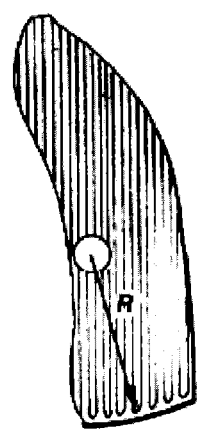
Figures 155, 156:
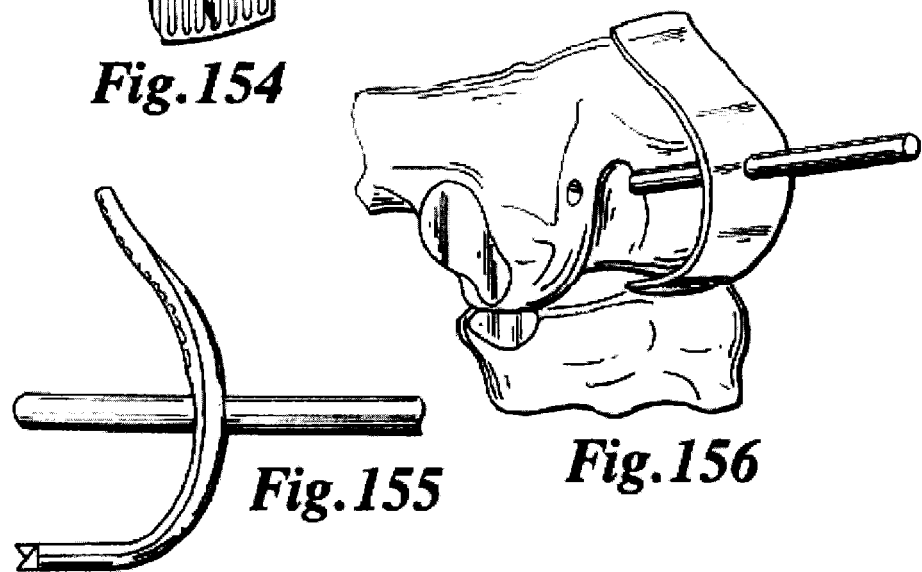
Figure 157:
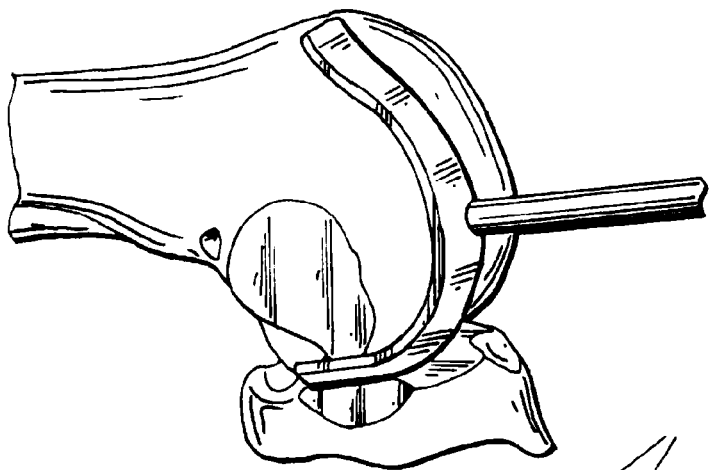
Figure 158:
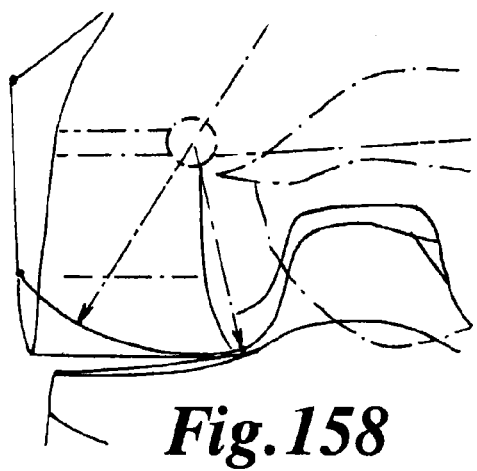
Figure 159:
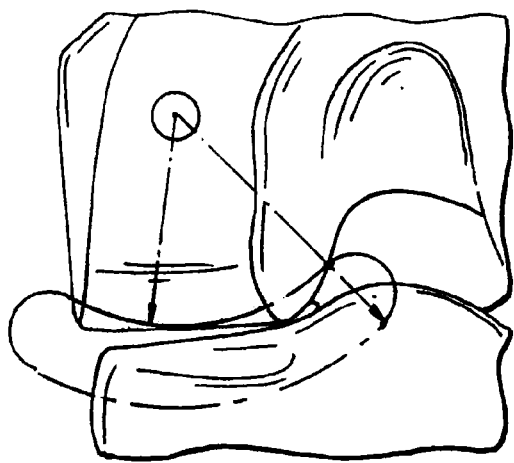
Figure 160:
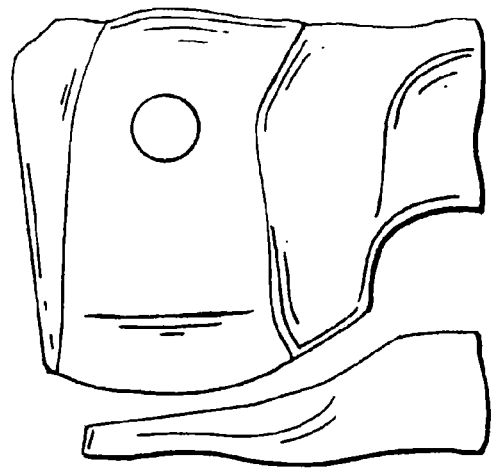
Figure 161:
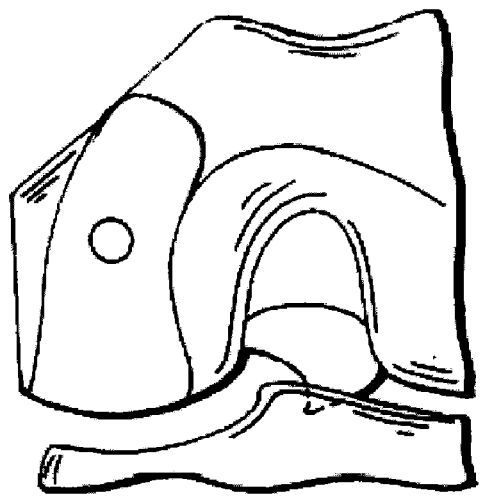

FIGS. 154 to 161 show an embodiment of the present invention for performing femoral resection with an oscillating, radiofrequency, or ultrasonic driver. The cutting tool shown in FIGS. 154 and 155 is rotated about the centerline of the shaft within a limited arc of motion, similar to an oscillating saw driver, however the direction of cutting is parallel to the drive axis of the saw driver rather than normal to it as is conventionally known. In this manner, the cutting tool is capable of creating resected geometries closely mimicking natural anatomic bone shapes while enabling the resection of bone through minimal surgical exposures. As shown in comparing FIGS. 158 through 161, instead of creating a flat posterior cut, this invention allows for the creation of cuts with a curved cutting profile. FIG. 161 represents the ability of this concept to be used to simultaneously make all tibial and femoral cuts in a single plunging motion, and that this would be attained simply by modifying the thickness of the posterior femoral cutting portion of the cutter by the amount indicated in FIG. 159, perhaps making the difference between the radius responsible for femoral resection geometry and the radius responsible to tibial resection geometry of around 5 mm to 15 mm for a Unicondylar replacement or 5 mm to 20 mm for cortical to conventional tricompartmental replacement. It should be noted that all of the femoral cuts, and optionally the proximal tibial cut, could be made in this manner and the location and orientation of the cuts would be based off of the guide hole shown in the distal femur in FIG. 56 for making with the shaft of the cutter. Alternatively, a shaft or other guide feature could be inserted into the distal femur and the cutting tool possess a mating female feature for that shaft. This invention offers significant improvements in both minimizing soft tissue displacement and intraoperative time savings as compared to the Oxford Unicondylar Instrumentation.

Figure 163:
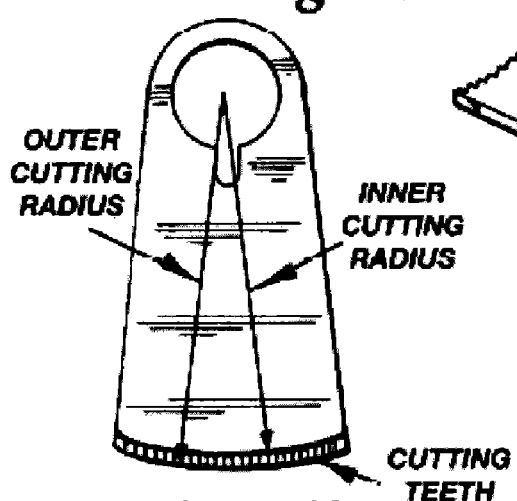
Figure 162:
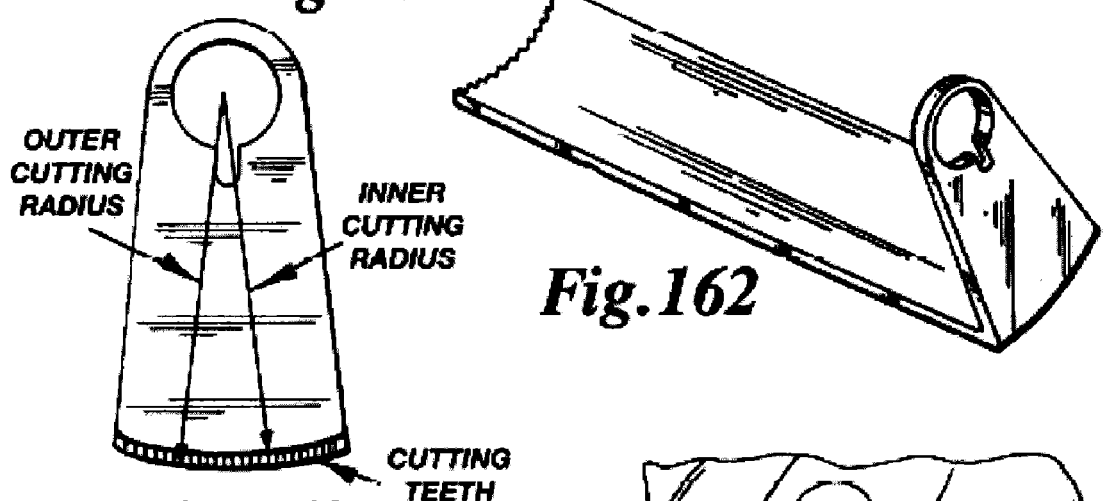
Figure 164:
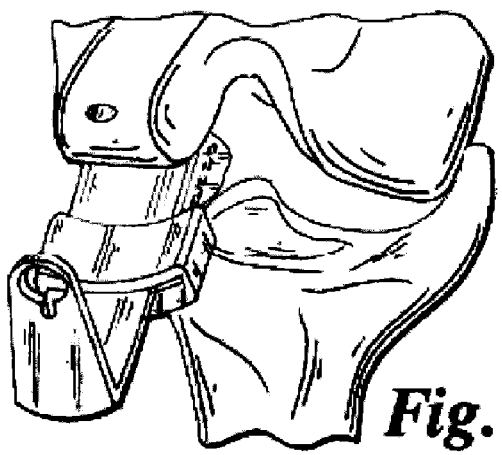
Figure 165:
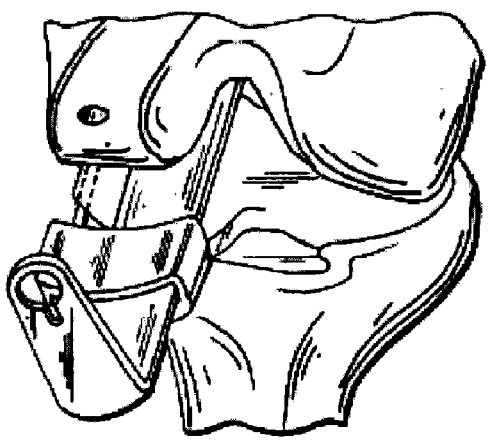
Figure 166:
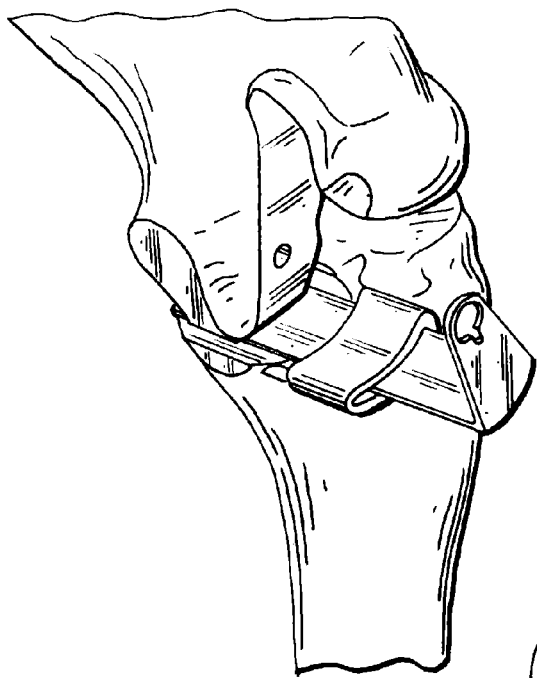
Figure 167:
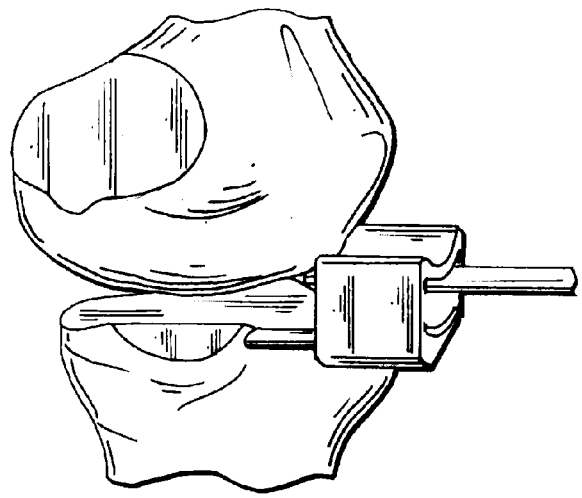
Figure 168:
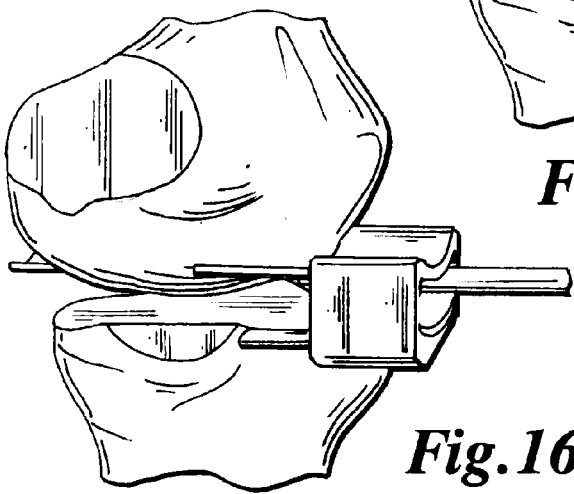

FIGS. 162 through 168 show an alternate but similar approach to the aforementioned. Instead of basing the control of the cutting tool on a guide feature formed or positioned on the femur, this embodiment of the present invention shows tibial resection, and alternatively both tibial and femoral resection, guided by a tibially mounted cutting guide or feature. Again, the cutting tool would be driven by a driver similar to an oscillating saw driver, although an alternative power means would be ultrasonically based to transmit ultrasonic energy along the length of the cutting tool to its curved or curvilinear cutting edge (it should be noted that in an ultrasonic embodiment, the cutting profile of the cutting tool may be other than a single arc). As shown in FIGS. 164 and 165, this could work well with a Pinplasty style guide, or could be optionally stabilized by implementation of Cam Pin Features disclosed in copending provisional applications, and could as shown in FIGS. 167 and 168, be used to cut both the tibia and the femur.

It is of particular interest to note that what is described as the Inner cutting radius and the outer cutting radius in FIG. 163 could be 'thickened' as was described for the femoral mounted embodiment to allow for resection of both the tibia and a single cut on the femur in one plunging motion. Alternatively, the cutter could be extended into the femur until the cutting profile of the cutting tool became tangent to the intended cutting path of the cuts to be made and the tibia manipulated to traverse a range of motion about the femur while cutting the femur while maintaining the cutting profile of the cutting tool tangent to the cutting path of the intended resected surface. This method is very applicable to the methods and apparatus described in the copending applications referenced herein, especially, Wireplasty resection and Pinplasty resection. Alternatively, a guide like the one shown in FIG. 168 could be used to incrementally form a series of discrete femoral cuts with the femur at different positions with respect to the tibia.

FIGS. 5 through 11

Figure 5:
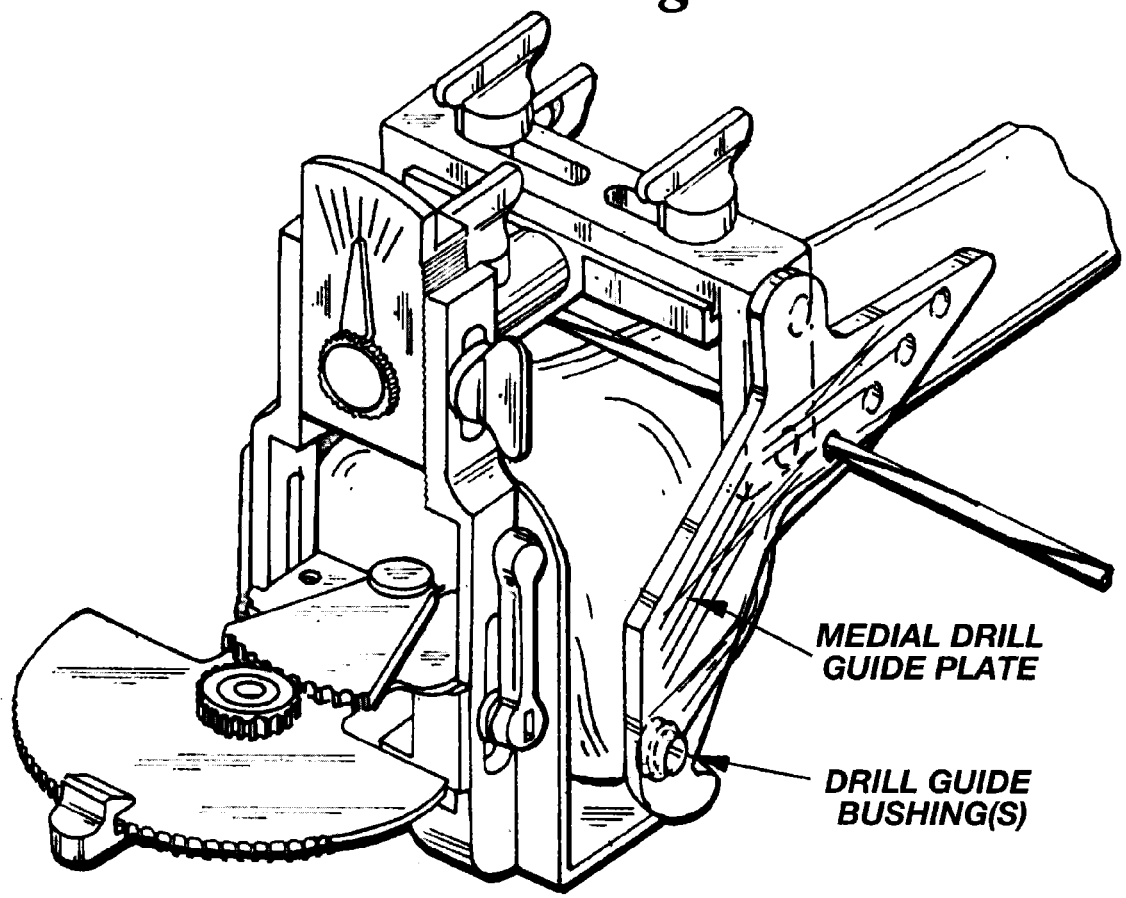
Figures 6, 7, 8:
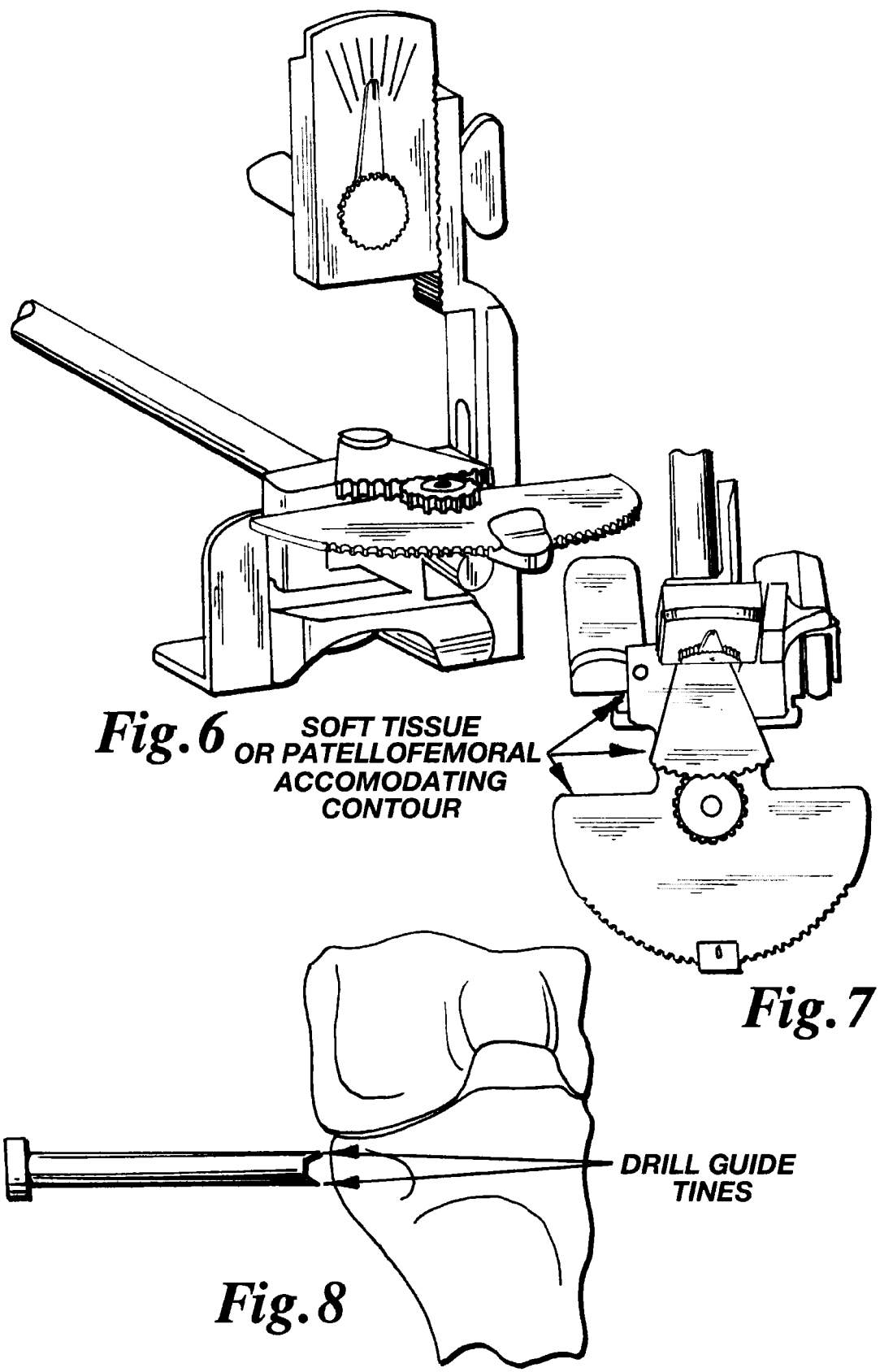

FIGS. 5 through 11 concentrate on alignment guide and/or drill guide techniques. FIG. 5 shows a manually operated alignment guide suitable for use with surgical exposures similar to that shown in FIG. 2 (it should be noted that surgical navigation sensors could be used to assist in determining final drill guide location and orientation). FIGS. 6 and 7 show an improvement upon the embodiment shown in FIG. 5 for enabling manual alignment guide use in less invasive incisions by providing soft tissue accommodating contours or reliefs. In other words, for a medial parapatellar incision, the alignment guide is configured to allow for appropriate contact and referencing of the distal and posterior femoral condyles, the IM canal (when not relying on an extramedullary reference or inference of the mechanical axis) or IM Rod, the anterior cortex or anterior runout point of a given or proposed implant size (via a stylus not shown), and the epicondylar axis via palpitation or visual reference while the patellar tendon, patella, and/or quadriceps tendon is draped over the lateral side (right side as shown in the figures) of the alignment guide allowing insertion of the guide when the patella is neither everted not fully dislocated as in conventional techniques. It should be noted that initial alignment indicated by reference of the distal femur may be further adjusted in all six degrees of freedom as a fine tuning for final cut location and orientation. This simply calls for the inclusion of additional adjustment of the location and orientation of the crossbar mechanism and/or rotational alignment arm, with respect to the initial reference provide for by contact between the body of the guide and the bone (optionally including the IM Rod), in flexion-extension angulation, varus-valgus angulation (rotational angulation and Anterior-Posterior location are already shown), mediolateral location (represented in this embodiment of the current invention by the cross bar mechanism in FIG. 5 where drill guide mediolateral location is shown as being independently and infinitely adjustable), and proximal-distal location (as shown in FIGS. 5, 6, and 7—it should be noted that this adjustment might be best embodied in an infinitely adjustable slide as opposed to the incrementally adjustable slide shown, and that simple marking would be present indicating the relative movement of the slide with respect to the body). It may be desirable to only utilize only a medial drill guide plate with multiple drill guide bushings to create holes extending partially or completely across the femur depending upon the manner in which the guides are to be connected to the femur.

FIGS. 8, 9, and 10 show an alternative alignment/drill guide embodiment of the present invention wherein a cannulated surgically navigated handle/drill guide is used to create fixation apertures in the bone for direct or indirect fixation of a cutting guide. As shown in FIG. 8, it may be advantageous to include tines for penetrating the bone to obtain initial stabilization of the handle in the location and orientation indicated by the surgical navigation system ("Surg Nav"—this term shall be used interchangeably with Computer Aided Surgical System or Image Guided Surgical System throughout this disclosure) prior to extending the drill, represented in FIG. 10, into the bone to create the aperture. An alternate feature to the tines shown could be a smooth but thin walled cylindrical edge of sufficient thinness or sharpness allowing it to cut and penetrate the bone to achieve initial stabilization prior to drilling. It should be noted that the aperture, or hole, thus created could be blind or extended to a specific depth, or optionally extended entirely through the bone and out the furthest side of the bone. Importantly, this process could be utilized transcutaneously through a small stab wound (perhaps 4 mm in length) through the skin to the bone surface, or through a preformed incision through which other instrumentation of the present invention or other devices including the prosthetic implant may be introduced during a procedure. Further, although only one cannulation is shown, a single handle may desirably contain multiple cannulations, some or all of which could be adjustably extended into contact with the bone to reduce any wandering of the drill contacting oblique bone surfaces and improve the precision and accuracy of aperture creation (thus allowing for the creation of apertures in the medial side of the femur, represented in FIG. 11, with a single Surg Nav Handle—Also, the apertures of the drill guide may be configured such that the femoral and tibial apertures shown in FIG. 11 are all created using a single positioning step for the handle). As represented in FIG. 9, there is very little distance over which the drill is cantilevered between its guidance within the cannulation(s) and its point of initial contact with the outer surface of the bone. This aspect of this embodiment of the current invention is critical in preserving the potential accuracy of Surg Nav systems, ie; the navigation system (the computer and the sensors) may be capable of determining appropriate location and orientation to +/−0.5 mm and +/−0.5 degrees, but if the location and/or orientation of the aperture created represents some path of least resistance in bone which is followed by the drill, the resultant location and orientation of cut surfaces, and thereby the location and orientation of the prosthesis attached thereto, will likely be seriously in error. At the end of the day, if the aperture creation step is not carefully controlled, you will have a very expensive alignment system whose stated purpose is to increase reproducibility, and whose method of implementation compromises this stated purpose.

It should also be noted that the methods described herein are applicable to the methods demonstrated in Provisional Patent Application Ser. No. 60/536,320 "Methods and Apparatus for Pinplasty Bone Resection", and Provisional Patent Application Ser. No. 60/540,992, entitled "Methods and Apparatus for Wireplasty Bone Resection."

Figures 88, 89:
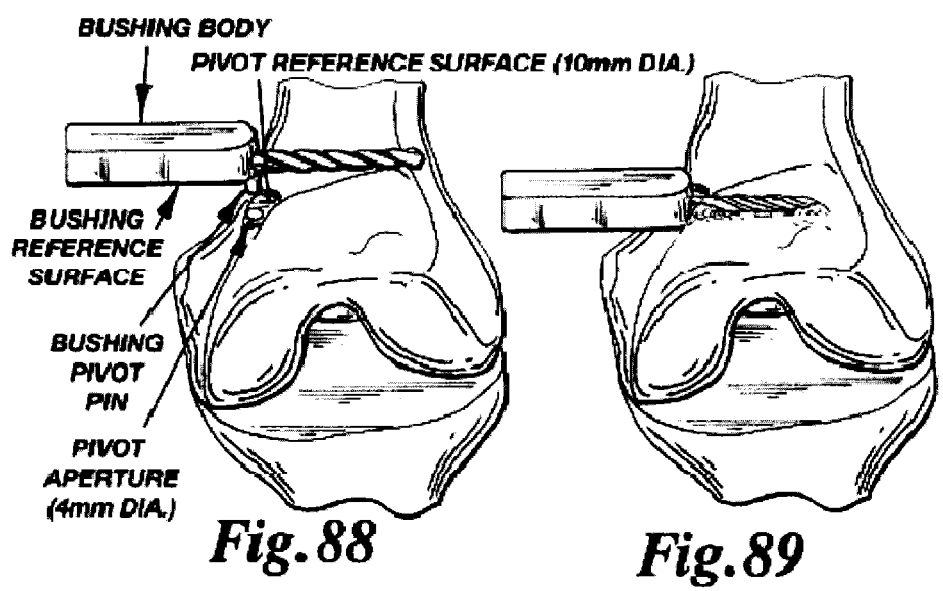
Figure 90:
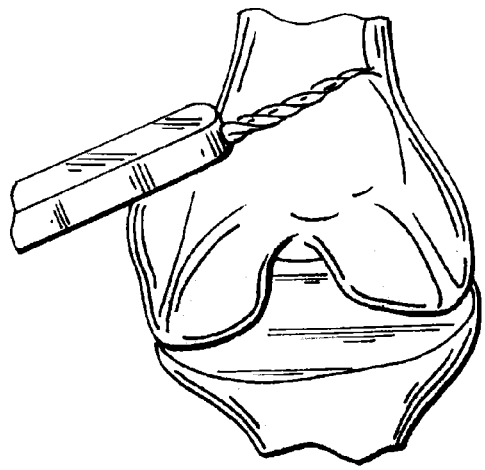
Figure 91:
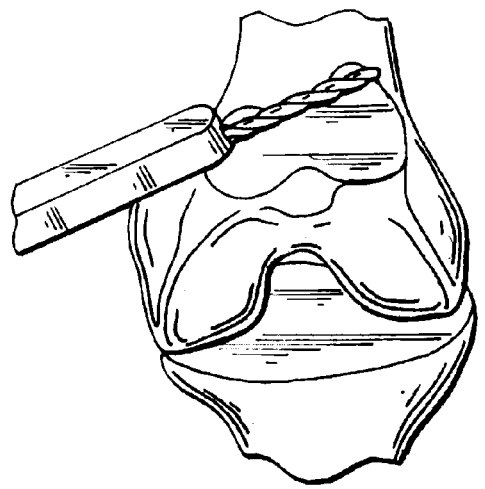
Figure 92:
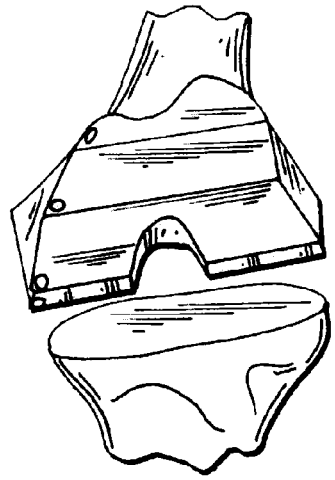
Figure 93:
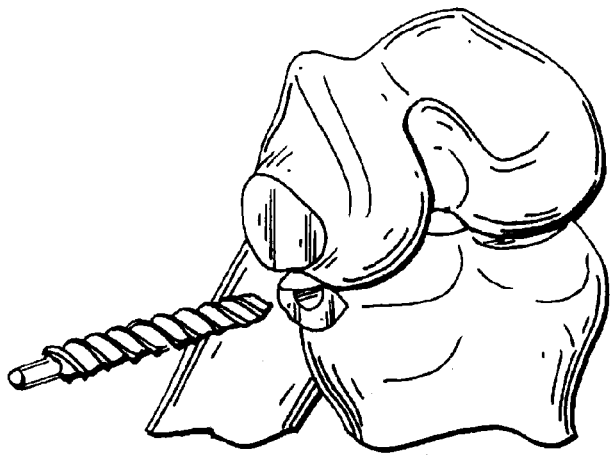

It should also be noted that another embodiment of the present invention, represented in FIGS. 88-92, benefits from the apparatus and principles of operation outlined above. As shown in FIG. 88, an aperture and a plane are created in bone which actually act as the cutting guide in controlling the location and orientation of the cutting tool within a specific plane during the creation of a cut surface. In this embodiment of the present invention, the cannulated drill guide will, in either manual or Surg Nav techniques, be used to guide a forstner style drill bit (the 'guide surface' shown in FIG. 88 could have been created by a modified drill with a leading section 15 mm long by 4 mm in diameter, responsible for the pivot aperture, and a 10 mm diameter following section which was about 10 mm long, responsible for the pivot reference surface) to create a larger diameter cylindrical aperture the bottom of which would define a pivot reference surface parallel to the cut surface to be created, and a smaller diameter cylindrical aperture to form a pivot aperture for maintaining the body of the bushing shown in FIGS. 88-91 in the proper location and orientation while cutting. Importantly, the technique outlined above is beneficially applied to tibial resection or any other planar or curvilinear resection technique as well.

Figure 104:
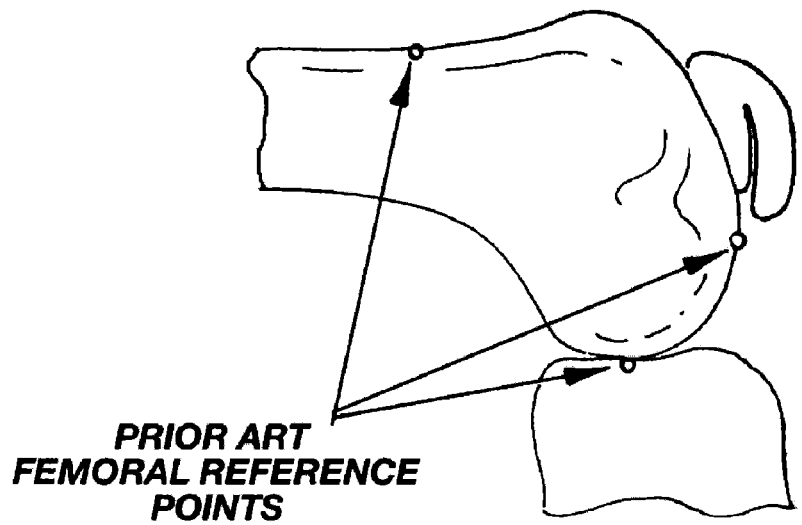
Figure 105:
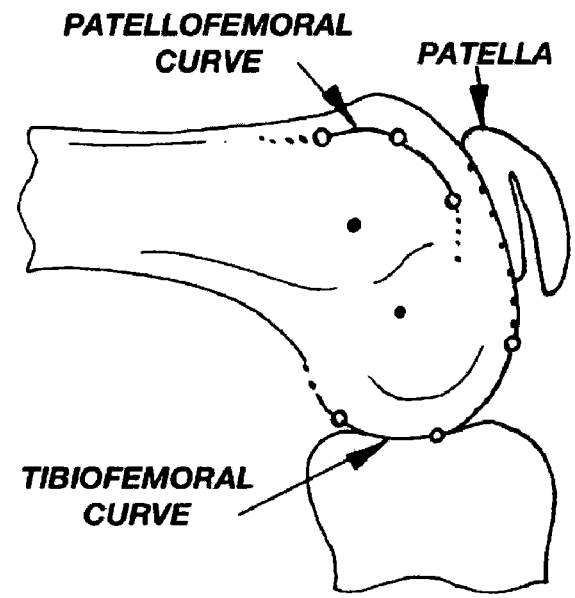
Figure 106:
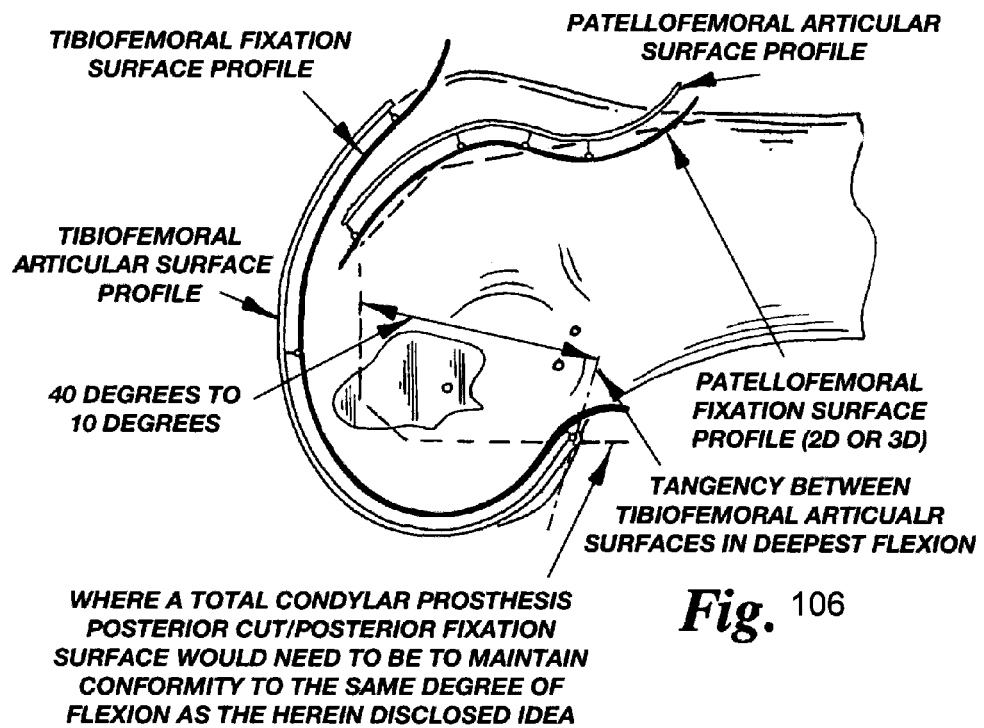
Figure 107:
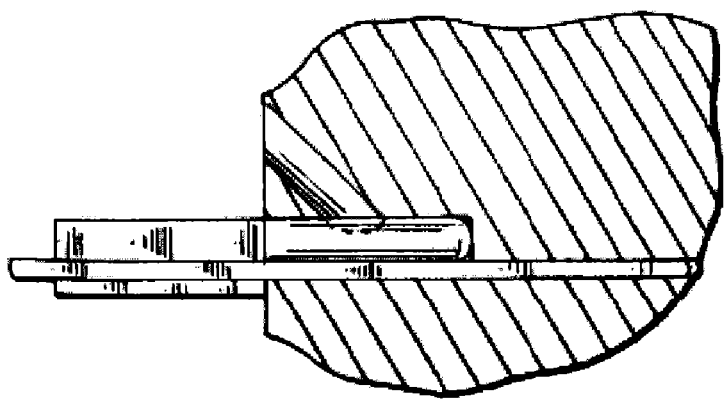

FIGS. 104 through 106 are an embodiment of the present invention that may prove to be a very usefully alternative to conventional rectilinear based referencing techniques. In essence, conventional alignment techniques, once having established appropriate flexion extension angulation and varus valgus angulation of desired implant location, reference the anterior cortex, distal most femoral condylar surface, and posterior most condylar surface (indicated in FIG. 105 by stars) to dictate the anterior posterior location, proximal distal location (otherwise known as distal resection depth), and appropriate implant size in determining the 'perfect' location and orientation for the appropriately sized implant (mediolateral location is normally 'eyeballed' by comparison of some visual reference of the mediolateral border surrounding the distal cut surface and some form of visual guide reference). These conventional techniques fail to directly reference the distinctly different anatomic bone features which dictate the performance of distinctly separate, but functionally interrelated, kinematic phenomena, and they also attempt to reference curvilinear articular surfaces by way of rectilinear approximations. The embodiment of the present invention is an alternative alignment technique with an object to overcome the errors inherent in prior art. As shown in FIG. 106, the femur possesses two distinct kinematic features and functions that lend themselves to physical referencing; the patellofemoral articular surface and the tibiofemoral articular surfaces, both of which are curved, more specifically these surfaces represent logarithmic curves that may be effectively approximated by arcs. The one codependency between the two articular functions, and therefore any geometric approximation made of them in referencing, is that they must allow for smooth kinematically appropriate articulation of the patella as it passes from its articulation with the trochlear groove (shown in blue in FIG. 106) to its articulation with intercondylar surfaces between the femoral condyles (shown in red in FIG. 106). Thus, knowing that three points define an arc and may be used to approximate a curve or sections of a curve, what is proposed is to use a referencing device which contacts at least one femoral condyle at three points to determine both an approximation of arc radius and centerpoint location, while independently or simultaneously referencing the trochlear groove at three points to determine both an approximation of arc radius and centerpoint location. The referencing system would further need to provide for the need of the articular surfaces of the trochlear articular surfaces to smoothly transition to those of the intercondylar surfaces. Armed with this information, a surgeon may most appropriately determine appropriate implant location and orientation.

This embodiment of the present invention is especially useful in determining the proper location, orientation, and implant size for modular tricompartment components, non-modular implants, and standard implants where the appropriate size, location, and orientation would be determined by that which best mimics existing articular bone surfaces thus resulting in optimal postoperative kinematic function. Alternatively, surgical navigation methods could be implemented in registering these articular surfaces and determining the resulting idealized implant location(s) and orientation(s) as reflected by the geometry and/or kinematics of the joint.

The following patents and patent applications describing various surgical navigation system and alignment and cutting guide systems that are beneficially utilized in whole or in part with the embodiments of the present invention are herein incorporated by reference: U.S. Pat. Nos. 2004/0122436, 2003/0069591, 2004/0039396, 2004/0153083, 5,810,827, 6,595,997, 2003/0069585, 2003/0028196, JP74214-2002, U.S. Pat. Nos. 2003/0208122, 6,725,080, 2004/0122305, 6,685,711, 2004/0153085, 2004/0152970, 6,694,168, WO04100758, WO04070580, WO04069036, U.S. Pat. Nos. 5,799,055, 6,236,875, 6,285,902, 6,340,363, 6,348,058, 6,430,434, 6,470,207, 6,477,400, 6,491,699, 6,697,664, 6,701,174, 6,711,432, 6,725,080, 6,796,988, and 6,827,723. Image guidance techniques typically involve acquiring preoperative images of the relevant anatomical structures and generating a data base which represents a three dimensional model of the anatomical structures. The relevant surgical instruments typically have a known and fixed geometry which is also defined preoperatively. During the surgical procedure, the position of the instrument being used is registered with the anatomical coordinate system and a graphical display showing the relative positions of the tool and anatomical structure may be computed in real time and displayed for the surgeon to assist the surgeon in properly positioning and manipulating the surgical instrument with respect to the relevant anatomical structure.

As is known in the art, the relevant dimensional data concerning an anatomical structure of interest, e.g., a femur, may be determined using data acquired from images of the anatomical structure to generate a data base representing a model of the anatomical structure. The model of the anatomical structure may be a three dimensional model which is developed by acquiring a series of two dimensional images of the anatomical structure. Alternatively, the model of the anatomical structure may be a set of two dimensional images having known spatial relationships or other data structure which can be used to convey information concerning the three dimensional form of the anatomical structure. The model of the anatomical structure may then be used to generate displays of the anatomical structure from various perspectives for preoperative planning purposes and intraoperative navigational purposes. A variety of technologies which may be employed to generate such a model of an anatomical structure are well known in the art and include computed tomography (CT), magnetic resonance imaging (MRI), positron emission tomography (PET), ultrasound scanning and fluoroscopic imaging technologies.

In one embodiment, the present invention contemplates a computer-based method of generating a surgical plan comprising reading digital data associated with a 3D (three-dimensional) model of a patient's bone, wherein the digital data resides in a memory in a computer; and generating a surgical plan for the patient's bone based on an analysis of the digital data associated with the 3D model. A surgical planner/simulator module in the computer assisted orthopedic surgery planner software makes a detailed surgical plan using realistic 3D computer graphics and animation. The simulated surgical plan may be viewed on a display seen of a personal computer. The planner module may also generate a pre-surgery report documenting various aspects of the bone surgery FIGS. 45 through 49 concentrate on mediolaterally, or 'side to side' oriented pins. Although any kind of cutting tool or milling handle could be engaged to these pins, a sagittal saw and an oscillating saw are shown. A wire or gigli saw could also be used in conjunction with the pins or guides disclosed herein as the cutting profile of such a saw affects the same linear cutting profile as a planar saw blade. Similarly, any of the following cutting tools effecting a linear cutting profile could also be used: rotating or oscillating or reciprocating cutters, linear milling tools, garrotes (thin, highly tensioned wire cutter), powered rasps or broaches, manual rasps or broaches, jack hammers, chisels, chain saws, osteotomes, abrasive wire cutters, oscillating/reciprocating/chain/gigli/coping/scroll/band/circular/hack/jig/sagittal saws, belt cutters, or cutting tools that combine elements of the aforementioned cutting tools.

In one embodiment, cutting tools may be plunged across, along, or through the pin guides of the present invention in any direction desirable. The directions of tool movement with respect to the pins include those generally oblique, normal, or parallel to the long axis of any pin, guide, or guide surface of this invention. Furthermore, the cutting tools may move linearly with respect to the bone and/or guide, or may be manipulated to move in circular, nonlinear, or 'sweeping motions.

Furthermore, although the pins can have the upper surface of the guide pins having been used to guide the cutting tool to create the cut surface, the pins could easily be located in a more anterior location allowing their 'underside' to act as the guide surface. This concept could be referred to as 'undercutting.' The technique of cutting while engaged to the 'upper side' of the pins could be referred to as 'overcutting' (a term not to be confused with removing too much bone).

FIGS. 45 through 49 show an alternative or adjunct/modular guide for use with the pins. This modular guide could be integrally formed with the pins or seperably attached thereto. The modular guide surfaces could help the surgeon initially align the cutting tool with respect to the pins and/or the cut to be created and/or also to maintain that relationship during a portion of or the entirety of the cutting process used to create the cut. Undercutting is also beneficial in this form of the present invention, as is the split pin, hollow pin, and hollow split pin embodiments of the present invention.

Figure 58:
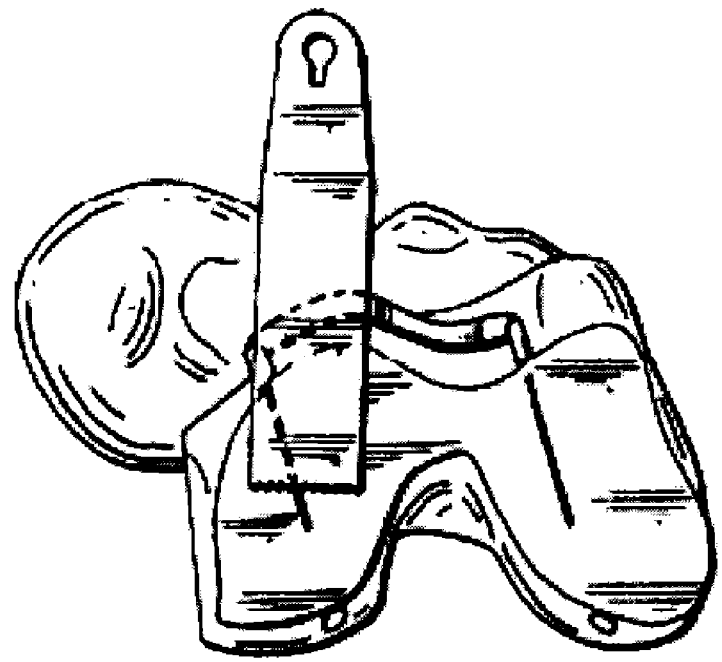

FIG. 58 shows that a cutting tool (in the instance shown, an oscillating saw blade) could be located, oriented, and/or moved/manipulated along, across, and/or through the pins/guides of the present invention in any manner desired.

Figure 108:
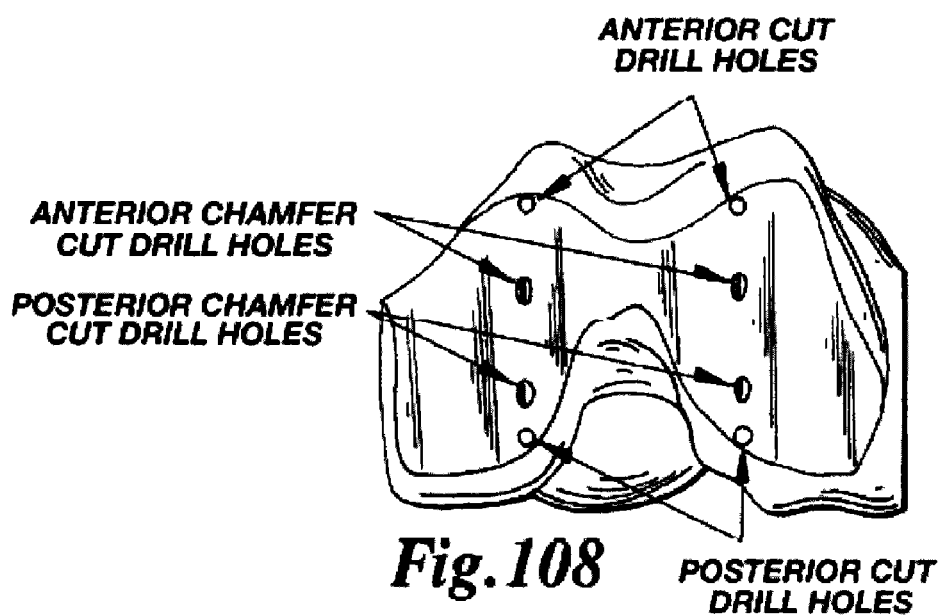
Figure 109:
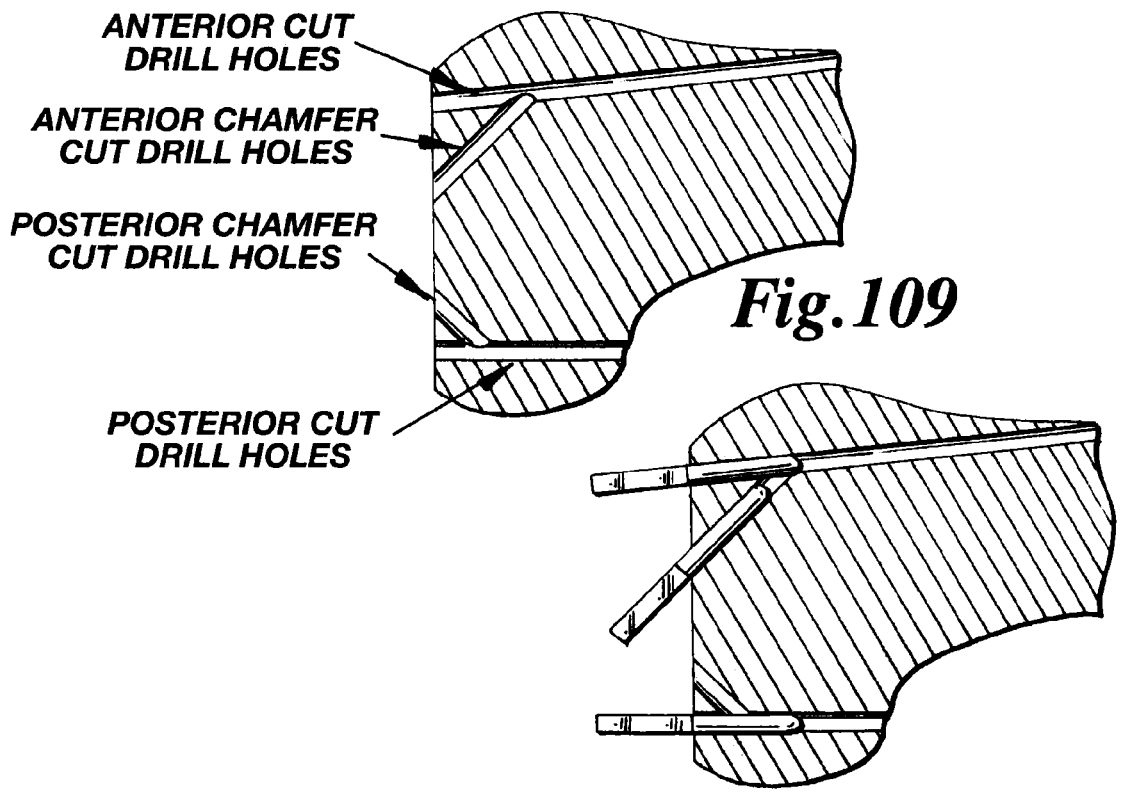
Figure 110:
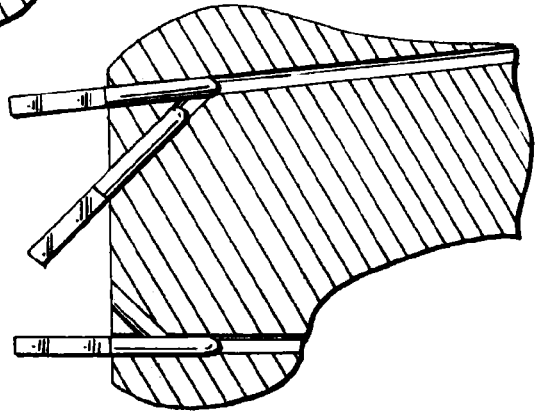
Figure 111:
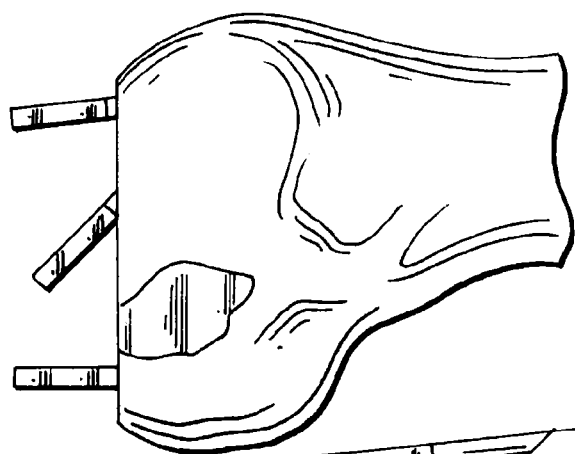
Figure 112:
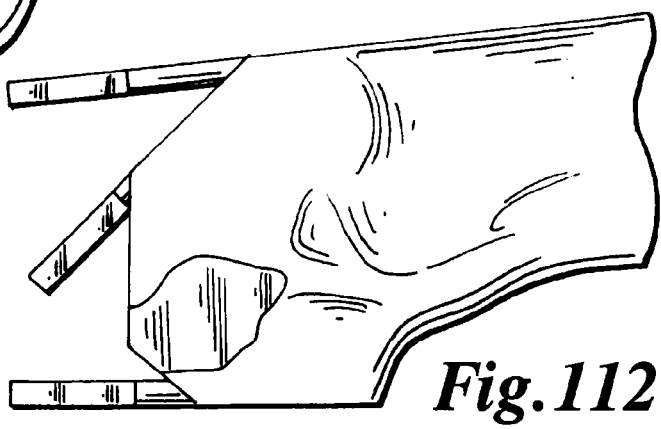
Figure 113:
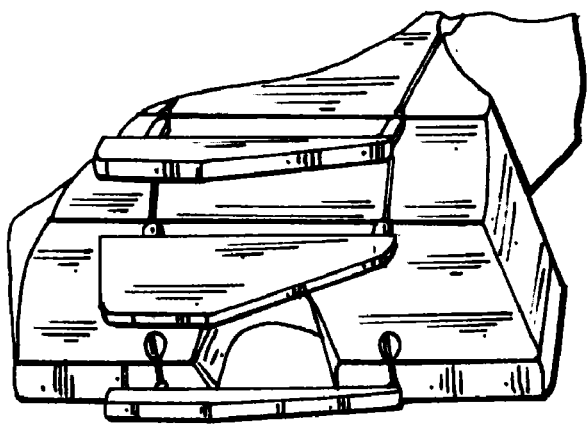
Figure 114:
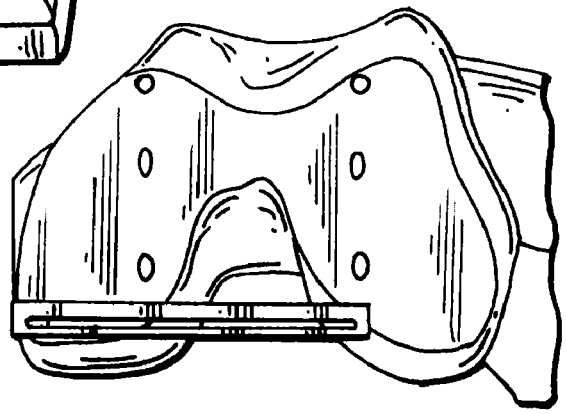
Figure 115:
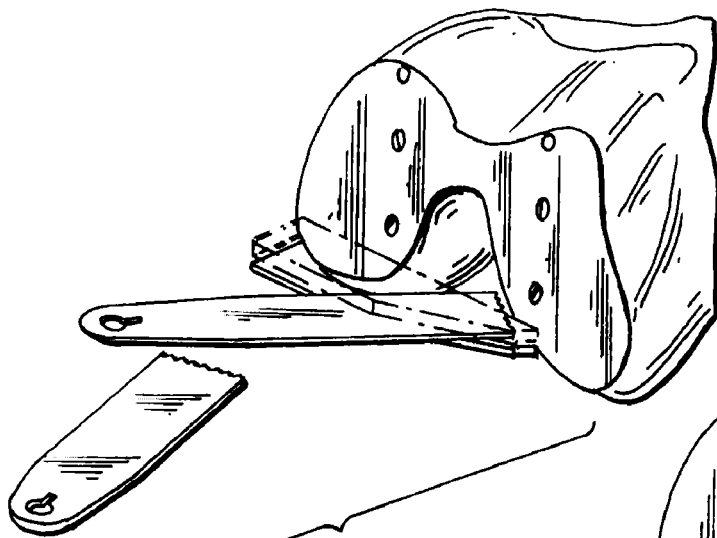
Figure 116:
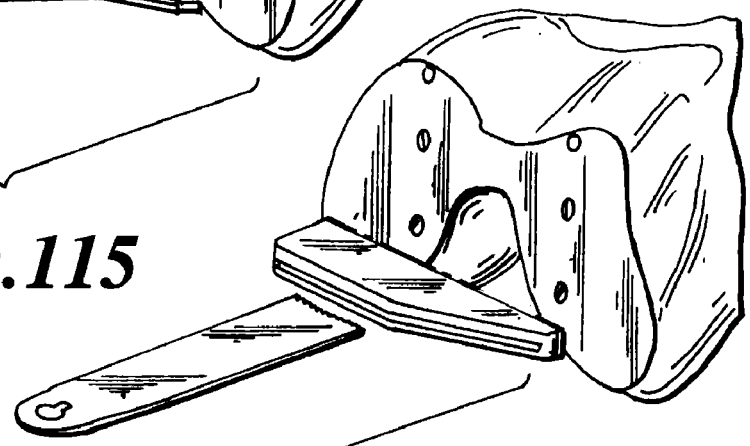
Figure 121:
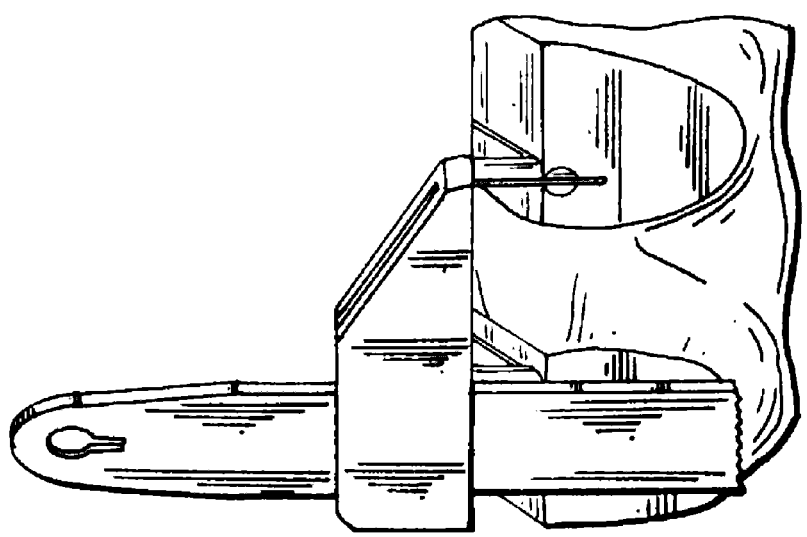

FIGS. 108 and 109 show the distal femur having been prepared to receive the cutting guide forms of the present invention that could be used to complete the remainder of the cuts. Beneficially, a single guide could be used to complete all the cuts by being incrementally attached to the bone at the appropriate locations as shown in FIGS. 107, 110 through 118, 120 and 121. Alternatively, a modified '4 in 1' cutting block designed to engage the pins of the present invention could be used. The modified '4 in 1' block could further be modified by being vertically cut in half and having the pins extending laterally of the block to provide guidance of the cutting tool laterally beyond the location of the conventional guide surfaces. FIGS. 114 through 121 show a capture feature added to the guides previously shown in FIG. 113. Note that FIG. 120 demonstrates that despite the abbreviation of the laterally located guide surfaces (to facilitate medial incision based procedure), the cutting tool remains robustly guided by the guide of the present invention when both the medial and lateral side of a bone is cut. Note that this design is shown to facilitate a medial approach and thus the guide has been 'medialized' to minimize necessary incision size--if a lateral approach were implemented, a 'lateralized' form of the present invention could be made available.

Figure 122:
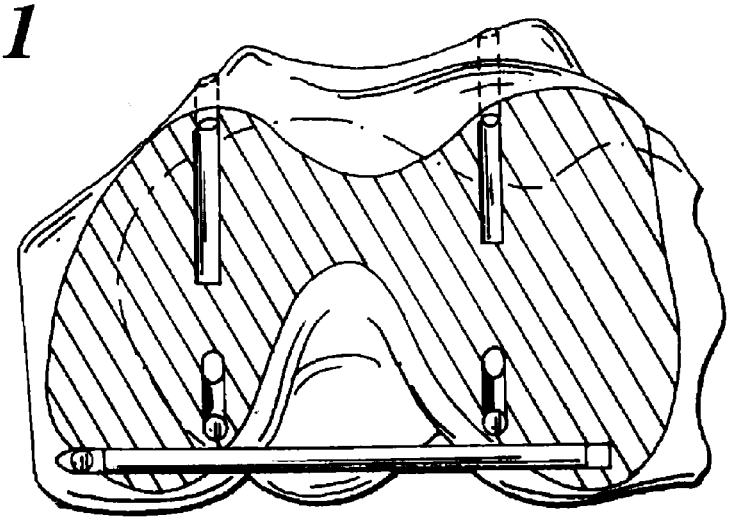
Figure 123:
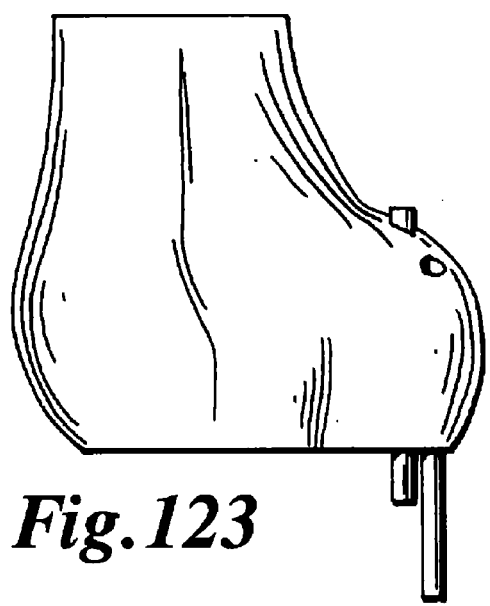
Figure 124:
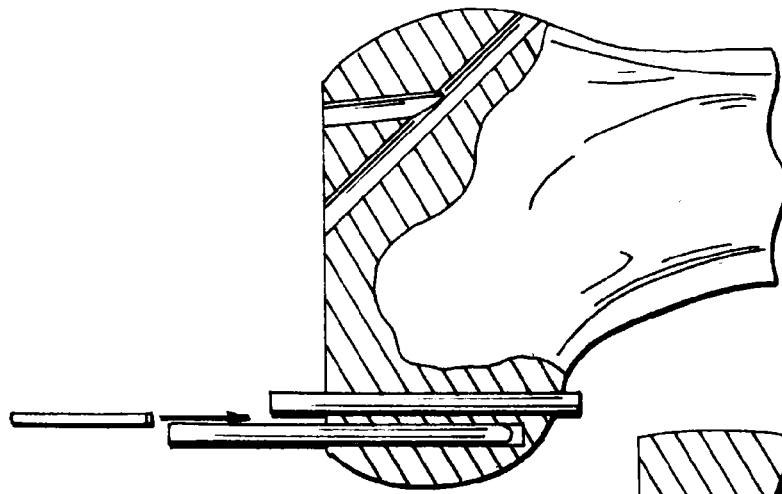
Figure 125:
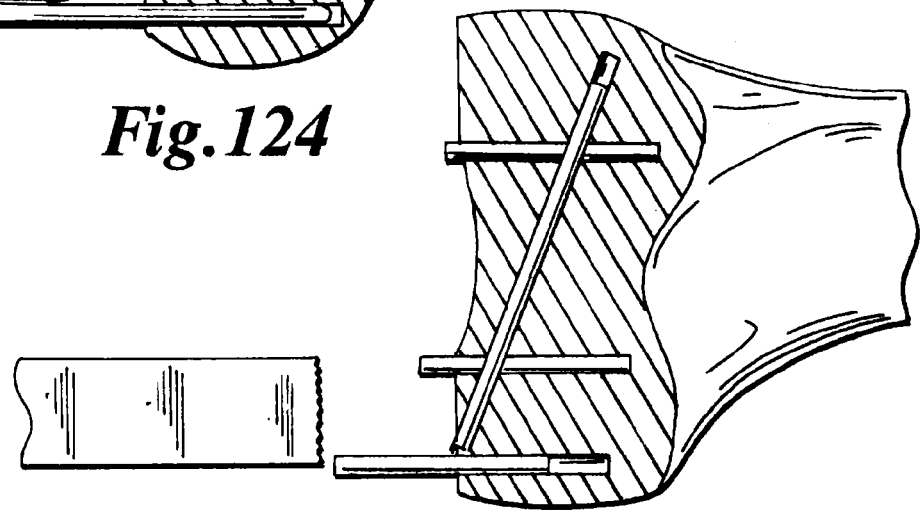
Figure 126:
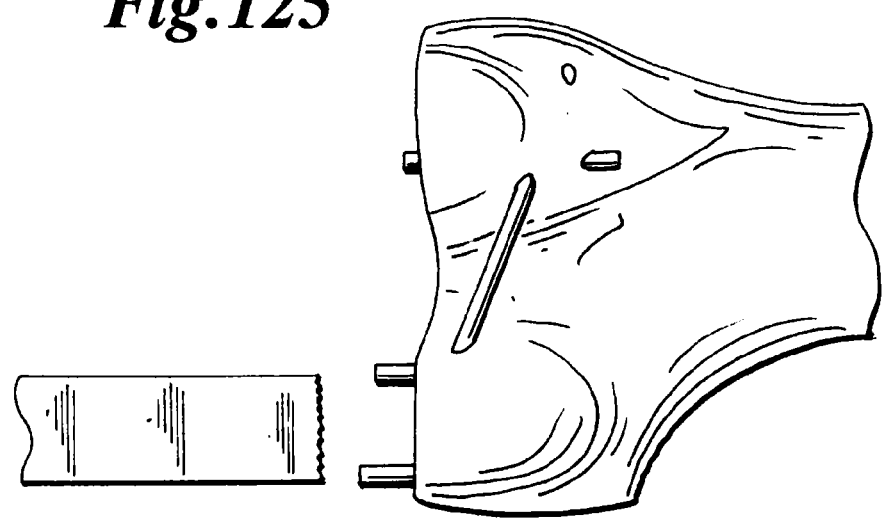
Figure 127:
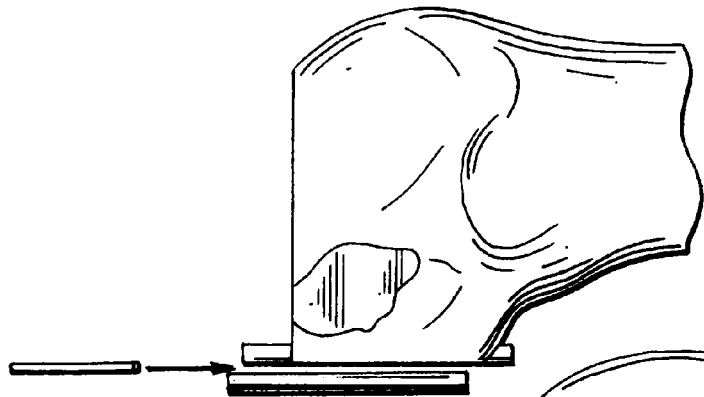

FIGS. 122 through 127 show some of the combinations of the forms of the present invention in use to complete the posterior cut. As shown in FIGS. 122, 125, and 127, two pins are located in overcutting mode, while two other pins are shown in undercutting mode. The combination of these pins acts to constrain motion of the cutting tool from traveling beyond the plane to be cut. For the sake of clarity, any combination of the forms of the present invention disclosed herein may be modified or combined to form constructs not specifically disclosed herein, but still within the scope of the present invention.

Figure 128:
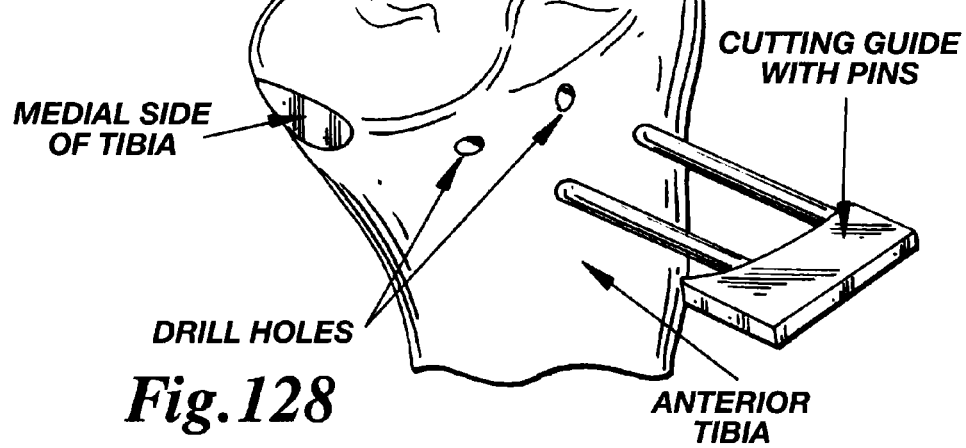
Figure 129:
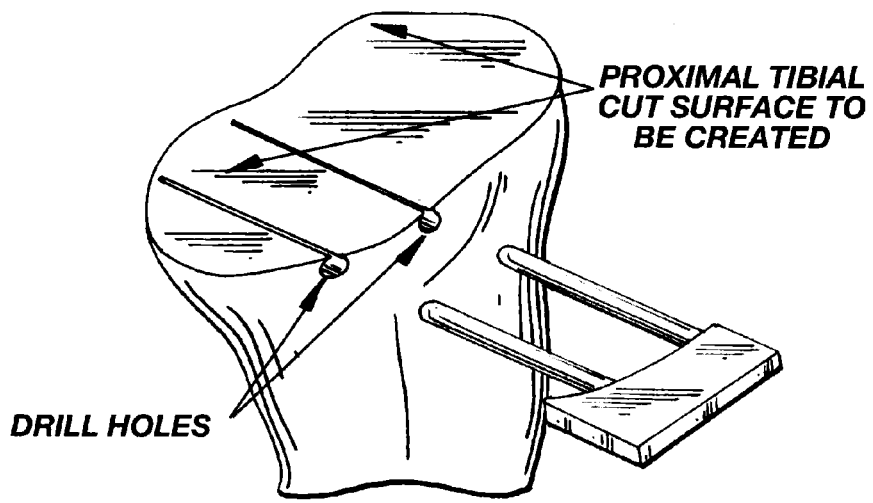

Tibial resection in TKA can be somewhat frustrating to a certain percentage of orthopedic surgeons. This frustration appears to stem from the high demands upon the surgeon's manual skills or craftsmanship. The forms of the present invention may help alleviate this issue by providing positive guidance of the cutting tool throughout all or most of the cutting process. Also, it should be noted that these concepts allow for implementation with very small incisions. FIGS. 128 through 130 forms of overcutting type pins/guides. Cutting tool captures are not shown, but could be seperably attached or formed integrally with the guide or pins. It is important to note the extent to which this and other forms of the present invention allow for contact with and guidance of the cutting tool. This creates a very stable surface for guiding the cutting tool. It should be noted that undercutting forms of the present invention could be used with guides or pins of similar configurations.

Preferably, pin guide members are made of materials that are more durable than bone material and also at least as durable, if not more durable, than the materials of the planar saw blade of the cutting tool. Materials could be harder or softer than the material comprising the cutting tool, and in some cases the cutting tool and the pins could be the same material--this is especially viable for ceramics which have very nice bearing characteristics. Certain surface treatments for metal may also be advantageous (titanium nitride, ceramic or non-metallic coating). Preferably, the cutting tool is prevented from cutting or abrading the cutting guide to avoid debris generation. Although pulsating lavage will normally clean any debris from the cut surfaces, the possibility of a foreign body, allergic, or other adverse reaction should be avoided. In certain situations, however, it may be desirable to construct the pin member guides of allograft or autograft bone tissue, such as when used in cortical bone tissue where it may be acceptable to cut the pin member guides. Diamond, or other carbon-based materials, could also be utilized, cost permitting. Also, the pin guides could be constructed of plastics, liquid metal, or some other form of injection moldable material thereby reducing cost levels to an extent enabling the pins to be offered on a disposable or semi-disposable basis.

FIGS. 172-176 show various depictions of the placement of pin members and operation of a cutting tool in accordance with alternate embodiments of the present invention.

Figure 172:
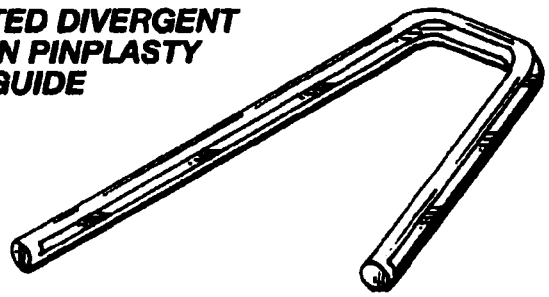
Figure 173:
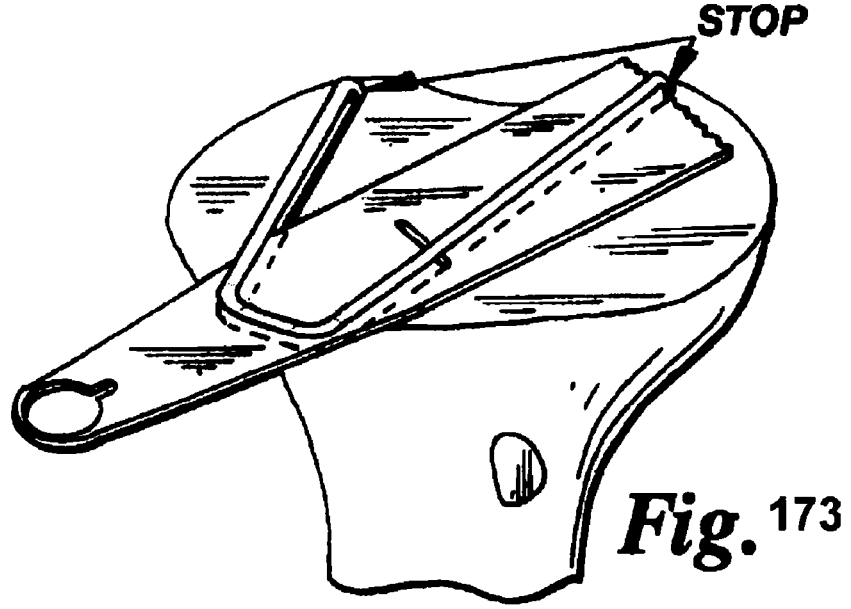

FIGS. 172 and 173 show yet another embodiment of the cutting guides of the present invention. This embodiment could be described as a hollow, divergent, split pin configuration cutting guide. In this embodiment of the present invention, the divergent angle of the pin axes are set to approximately 20 degrees, but divergent angles of up to 130 degrees are considered to be within the scope of the present invention as are pins that coact to form axes that intersect within the border of the resected surface(s) to be created as viewed from a direction normal to the resected surface to be created. One feature of critical benefit to MIS procedures with respect to this embodiment of the present invention is the ability of the split pin to incorporate a stop feature (as shown in FIG. 172) where critical structures such as ligaments, tendons, capsule, veins, arteries, or nerves may be prevented from direct contact with the cutting tool's cutting surfaces by limiting the depth to which the cutting tool may be extended in the direction of those critical structures prior to contacting the stop feature. Another important feature of this embodiment of the present invention is the flexibility of the divergent guide that enables the cutting guide to be squeezed by the surgeon to initially line up and insert the tips of the pin features into the divergent apertures and then push the pins into the location desired. It should also be noted that the two divergent pins could be constructed as independent constructs as opposed to the unitary structure shown in FIG. 172 and optionally provide features for attachment of a bridging feature.

Figure 174:
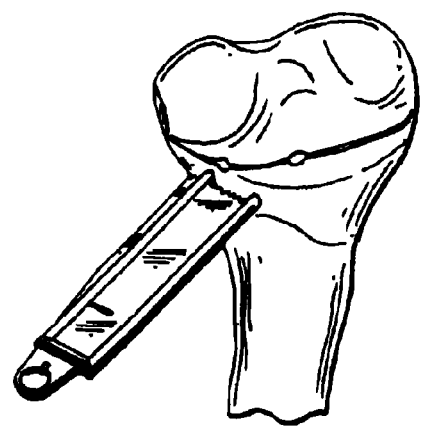
Figure 175:
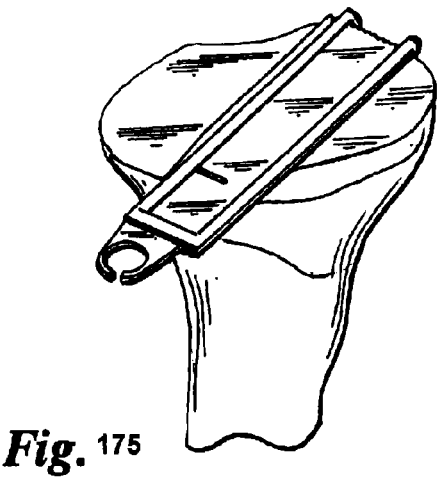
Figure 176:
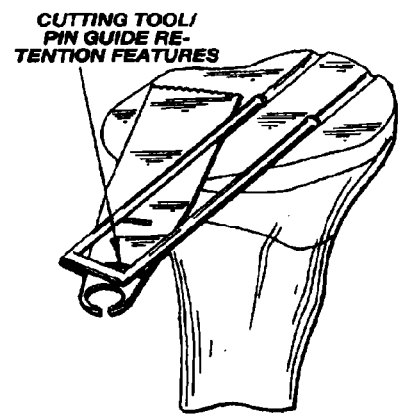

FIGS. 174, 175, and 176 show an embodiment of the present invention that in essence provides for the apertures formed in the bone to act as the cutting guide in coacting with a carriage linked to a saw blade or other cutting tool. Beneficially, the saw blade and carriage (hereinafter referred to as the "cutting tool/pin guide") may be packaged together as an assembly intended for single use only, or a limited number of uses, and/or as sterile or non-sterile. In essence, the retention feature of the cutting tool/pin guide enables the cutting tool and carriage components to coact to continuous guide the cutting tool as it traverses the surfaces within, along, and about the apertures formed in the bone to create the resected surfaces with respect to which the implant is to be fixed. This embodiment also possesses an effective stop feature preventing the cutting teeth from inducing catastrophic damage to soft tissue structures.

Figure 171:
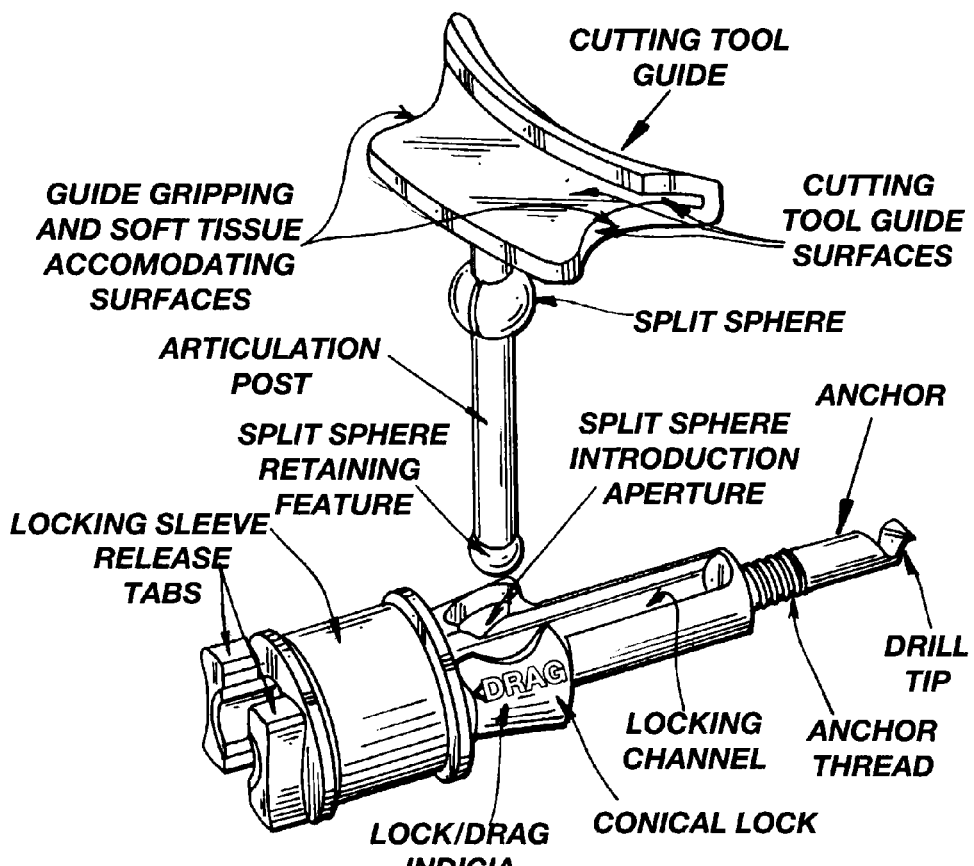

FIG. 171 describes another embodiment of the present invention. The device overcomes the drawbacks of the inability to easily and accurately secure existing alignment or guide systems to a desired location or position, a problem often referred to as the fiddle factor problem. The fiddle factor problem extends intraoperative time, creates surgeon frustration and can lead to implant mal-alignment due to inaccurate alignment guide or cutting guide positionings.

An example of the fiddle factor problem in existing alignment and guide systems is shown, for example, in the device by Grimm described in U.S. Patent Publ. No. 2004/0122436 (herein incorporated by reference). The actuation of the locking mechanism to fix the carriage with respect to the sphere will actually cause the carriage to rotate with respect to sphere. Thus in use, the surgeon would attain the correct location and orientation of the cutting tool guide of Grimm, as indicated on the computer display, and then attempt to lock varus valgus, flexion extension, and internal/external rotational alignment by way of the actuation of locking mechanism, but in doing so, the carriage, and thereby the cutting tool guide would shift from the desired orientation. This dynamic will force the surgeon to iteratively tighten the lock, adjust the carriage, tighten the lock a little more, adjust the carriage a little more, tighten the lock even more, adjust the carriage a little more, etc., until intraoperative time constraints would compel the surgeon to move forward with the procedure with alignment that is suboptimal. These problems can be compounded by several additional adjustments and locking mechanisms to similarly fiddle that need to be made prior to making the first cut.

Simply put, the major problem with the majority of surgically navigated "anchor-cutting guide linkage" type devices is that the act of locking the orientation and location of the cutting guide in place with respect to the anchor and/or the desired implant location and orientation actually causes the location and orientation of the cutting guides to change, in some cases radically. As the ultimate objectives of surgical navigation are to improve accuracy and promote and facilitate minimally invasive implantation, the fiddle factor problem clearly runs counter to these objectives.

This embodiment of the present invention solves the fiddle factor problem by providing for an elegant locking mechanism that secures a plurality of translation and rotational degrees of freedom in a manner which fails to shift the location and orientation of the cutting tool guide while it is being secured. More precisely, the sum of the force moment couples acting about the center of mass of the cutting tool guide(s) by the actuation of the locking mechanism are governed by the following equation: $\Sigma M_{(x,y,z)} + \Sigma F_{(x,y,z)} = 0$ (1), where M=moments about three mutually orthogonal axes and F=forces about three mutually orthogonal axes.

The primary components of this embodiment of the present invention are shown in FIG. 171. These include the anchor, the locking sleeve, the split sphere, the cutting tool guide and the Surgical Navigation Sensor (not shown for the sake of clarity and will herein be referred to simply as a "sensor").

The anchor possesses four primary features, either alone or in combination with the primary components of this embodiment of the present invention. Those features include a bone penetrating and anchor stabilizing feature (indicated as the anchor thread in FIG. 171 and the drill tip in FIG. 171), a locking feature (indicated as the conical lock in FIG. 171), a linkage engagement feature (indicated as the locking channel in FIG. 171), and a quick release feature (indicated as the release tabs in FIG. 171). In use, the anchor may be drilled into and fixed to a face of the bone in one continuous or semi-continuous step, or an aperture may be predrilled to which the anchor is subsequently fixed. If pre-drilling is used, a simple template (not shown) including a faux guide surface, drill guide aperture, and handle may be used for the purpose of facilitating the surgeon's "eyeball" placement of the pre-drilled aperture; in other words, the faux guide surface acts as a general indication of where the surgeon thinks the cut is to be located simply based on how it looks relative to the bone based on the surgeon's judgment/experience to facilitate pre-drilled aperture placement for the anchor enabling minimal adjustment of the cutting tool guide with respect to the anchor.

The locking sleeve possesses three primary features alone or in combination with the primary components of the embodiment of the present invention including a drag feature, a locking feature, and a surgeon grasping surface. These features coact to enable rapid and effective locking and quick release of the cutting tool guide with respect to the anchor. The drag feature coacts with the anchor, split sphere, and cutting tool guide to affect frictionally resisted movement of the cutting tool guide with respect to the anchor about 3, 4, 5, 6, 7, or 8 degrees of freedom.

The split sphere, in this embodiment of the invention, possesses three primary features alone or in combination with the primary components of the embodiment of the present invention including an articulation aperture feature, a spherical articulation feature, and a relief feature. As may be seen in FIG. 171, the articulation aperture feature of the split sphere coacts with the articular post of the cutting tool guide to enable frictionally resisted movement and frictionally affected locking of the cutting guide with respect to the split sphere. When enabling frictionally resisted movement (herein described as "drag mode"), the amount of force against which this mechanism must resist movement of the cutting tool guide with respect to the anchor is at least equivalent to the force affected by way of gravity, and in preferred embodiments, is at least equivalent to the combination of force affected by gravity and the force affected by soft tissue contacting the device. When enabling frictionally affected locking (herein described as "locking mode"), the amount of force against which this mechanism must resist movement of the cutting tool guide with respect to the anchor, in a preferred embodiment, is at least equivalent to the force moment couples the applied to the device by the combination of gravitational, soft tissue, and cutting tool contacting forces. To further facilitate the effectiveness of these modes, the internal and external surfaces of the split sphere, and optionally the features of the present invention that come into contact with them, are textured to facilitate robust fixation. Such textures include, but are in no way limited to, #7 to #20 grit blast, Tecotex.TM., knurling, and other means known in the art for effectively increasing the surface area of a smooth surface.

The spherical articulation feature of the split sphere enables both tri-axial rotational and single axial translational manipulation of the split sphere with respect to the anchor and along its long axis, as well as simultaneous locking of those degrees of freedom, and an additional axial translational degree of freedom of the articulation post of the cutting tool guide with respect to the articulation aperture feature of the split sphere. Locking is attained by compression of the locking channel feature (see FIG. 171) of the anchor against the spherical articulation feature and, by way of the relief feature of the split sphere, the articulation post feature of the cutting tool guide. The relief feature of the split sphere enables two distinct functions. The relief feature enables elastic compression of the split sphere against the articulation post of the cutting tool in response to force applied to the split sphere by the locking channel feature in response to actuation of the conical lock feature.

In the context of tibial resection for the embodiment of the present invention, the sphere articulates with respect to the anchor in 4 degrees of freedom (anterior to posterior, varus-valgus, internal external rotation, and flexion-extension) while the articulation post, and thereby the cutting tool guide, articulate with respect to the split sphere, and thereby the anchor and bone, in at least one additional degree of freedom (proximal-distal). The second function of the relief feature is to optionally allow the articulation post of the cutting tool guide to be rotationally keyed to the split sphere to enable the split sphere and cutting tool guide to be rotated in tandem with respect to the locking channel of the anchor.

In another embodiment of the present invention (not shown), the articulation post of the cutting tool guide could be split along its long axis and coact with an articulation feature on the cutting tool guide to enable mediolateral translation and locking of the cutting tool guide with respect to the bone wherein effective locking of the mediolateral degree of freedom would also be affected by actuation of the cone lock feature in addition to the aforementioned 5 degrees of freedom.

The complete disclosures of the patents, patent applications and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein.

What is claimed:

1. A method for providing instrumentation, implants, and information for a total knee arthroplasty procedure comprising:

providing a total knee arthroplasty femoral implant and a distal femoral cutting guide, the distal femoral cutting guide having a slot adapted to guide and receive an oscillating sawblade to create a distal cut on a distal end of a distal femur, the distal cut having a curvilinear shaped anterior periphery, the slot having a curvilinear shaped posterior periphery substantially matching the shape of the anterior periphery of the distal cut, wherein the shape of the posterior periphery of the slot is based upon preoperatively acquired digital image data;

providing a surgeon with information on a method to perform the total knee arthroplasty procedure using the distal femoral cutting guide, the oscillating sawblade, and the femoral implant, the method including:

positioning the distal femoral cutting guide against the femur immediately adjacent the anterior periphery of the distal cut to be made, engaging the sawblade with the slot, and creating the distal cut on the femur using the slot to operably guide the sawblade;

prior to creating the distal cut, creating markings in the distal end of the femur using a marking element;

removing the distal femoral cutting guide after creating the distal cut on the femur and disposing of the distal femoral cutting guide so that it is not used as a part of another total knee arthroplasty procedure;

following removal of the distal femoral cutting guide, attaching a second cutting guide to the femur, wherein an anterior to posterior location and an internal-external orientation of the second cutting guide is determined by operably referencing the markings on the femur;

using the second cutting guide to create at least two of an anterior cut, an anterior chamfer cut, a posterior chamfer cut, and a posterior cut on the distal femur; and implanting the femoral implant on the distal femur.

2. The method of claim 1, wherein the marking element is one of a pin, a nail, a screw, or a drill and the second cutting guide references one of an aperture created in bone by at least one of the marking elements or at least one marking element.

3. The method of claim 1, wherein the step of using the second cutting guide includes using the second cutting guide to create the anterior cut, the anterior chamfer cut, the posterior chamfer cut and the posterior cut.

4. The method of claim 1, further comprising providing an alignment guide and wherein the method with which the surgeon is provided with information further includes:

positioning the alignment guide on the distal femur of the patient, the alignment guide conforming to the shape of the femur and positioned based on digital preoperative patient data such that the alignment guide simultaneously contacts the femur at least at nine points along an anterior to posterior curvature of the femur that includes at least three points on a non-resected medial femoral condyle spanning a substantial portion of an anterior to posterior kinematic path of a portion of a tibia about the femur, at least three points on a non-resected lateral femoral condyle and at least three points on a non-resected patellofemoral articular surface of the femur, and wherein the alignment guide operably dictates the location and orientation of both the distal cutting guide and the second cutting guide.

5. The method of claim 1, wherein at least one of the distal femoral cutting guide and the second cutting guide is constructed of a polymer material.

6. The method of any one of claims 1-4, wherein the distal femoral cutting guide is at least partially constructed of a polymer material and wherein the distal femoral cutting guide includes one of a metallic or ceramic guide element forming a bearing surface at least partially located within the slot and the step of creating the distal cut on the femur utilizes the bearing surface to guide the saw blade.

7. The method of claim 6, wherein the distal femoral cutting guide further comprises a saw blade stop feature defining a location beyond which the saw blade is not intended to extend and the step of creating the distal cut on the femur further comprises positioning the saw blade stop feature at the location beyond which the saw blade is not intended to extend such that the saw blade stop feature is positioned to prevent the saw blade from extending beyond the location.

8. The method of one of claims 2 and 3, further comprising providing an alignment guide and wherein the method with which the surgeon is provided with information further includes:

positioning the alignment guide on the distal femur of the patient, the alignment guide conforming to the shape of the femur and positioned based on digital preoperative patient data such that the alignment guide simultaneously contacts the femur at least at nine points along an anterior to posterior curvature of the femur that includes at least three points on a non-resected medial femoral condyle spanning a substantial portion of an anterior to posterior kinematic path of a portion of a tibia about the femur, at least three points on a non-resected lateral femoral condyle and at least three points on a non-resected patellofemoral articular surface of the femur, and wherein the alignment guide operably dictates the location and orientation of both the distal cutting guide and the second cutting guide.

9. A method for performing a total knee arthroplasty procedure comprising:

positioning a distal femoral cutting guide against a femur immediately adjacent an anterior periphery of a distal cut to be made on a distal end of the femur, the distal femoral cutting guide having a slot adapted to guide and receive an oscillating sawblade to create the distal cut, the anterior periphery of the distal cut having a curvilinear shape, and the slot having a posterior periphery having a curvilinear shape substantially matching the shape of the anterior periphery of the distal cut, wherein the shape of the posterior periphery of the slot is based upon preoperatively acquired digital image data;

engaging the sawblade with the slot and creating the distal cut on the femur using the slot to guide the sawblade;

prior to creating the distal cut, creating markings in the distal end of the femur using a marking element;

removing the distal femoral cutting guide after creating the distal cut on the femur and disposing of the distal femoral cutting guide so that it is not used as a part of another total knee arthroplasty procedure;

following removal of the distal femoral cutting guide, attaching a second cutting guide to the femur, wherein an anterior to posterior location and an internal-external orientation of the second cutting guide is determined by operably referencing the markings on the femur;

using the second cutting guide to create at least two of an anterior cut, an anterior chamfer cut, a posterior chamfer cut, and a posterior cut on the distal femur; and implanting a femoral implant on the distal femur.

10. The method of claim 9, wherein the marking element is one of a pin, a nail, a screw, or a drill and the second cutting guide references one of an aperture in bone created by at least one of the marking elements or at least one marking element.

11. The method of claim 9, wherein the step of using the second cutting guide includes using the second cutting guide to create the anterior cut, the anterior chamfer cut, the posterior chamfer cut and the posterior cut.

12. The method of claim 9, further comprising:

positioning an alignment guide on the distal femur of the patient, the alignment guide conforming to the shape of the femur and positioned based on digital preoperative patient data such that the alignment guide simultaneously contacts the femur at least at nine points along an anterior to posterior curvature of the femur that includes at least three points on a non-resected medial femoral condyle spanning a substantial portion of an anterior to posterior kinematic path of a portion of a tibia about the femur, at least three points on a non-resected lateral femoral condyle and at least three points on a non-resected patellofemoral articular surface of the femur, and wherein the alignment guide operably dictates the location and orientation of both the distal cutting guide and the second cutting guide.

13. The method of claim 9, wherein at least one of the distal femoral cutting guide and the second cutting guide is constructed of a polymer material.

14. The method of any one of claims 9-12, wherein the distal femoral cutting guide is at least partially constructed of a polymer material and wherein the distal femoral cutting guide includes one of a metallic or ceramic guide element forming a bearing surface at least partially located within the slot and the step of creating the distal cut on the femur utilizes the bearing surface to guide the saw blade.

15. The method of claim 14, wherein the distal femoral cutting guide further comprises a saw blade stop feature defining a location beyond which the saw blade is not intended to extend and the step of creating the distal cut on the femur further comprises positioning the saw blade stop feature at the location beyond which the saw blade is not intended to extend such that the stop feature is positioned to prevent the saw blade from extending beyond the location.

16. The method of one of claims 10 and 11, further comprising:

positioning an alignment guide on the distal femur of the patient, the alignment guide conforming to the shape of the femur and positioned based on digital preoperative patient data such that the alignment guide simultaneously contacts the femur at least at nine points along an anterior to posterior curvature of the femur that includes at least three points on a non-resected medial femoral condyle spanning a substantial portion of an anterior to posterior kinematic path of a portion of a tibia about the femur, at least three points on a non-resected lateral femoral condyle and at least three points on a non-resected patellofemoral articular surface of the femur, and wherein the alignment guide operably dictates the location and orientation of both the distal cutting guide and the second cutting guide.

17. A method for implanting a total knee arthroplasty femoral implant comprising:

providing the femoral implant;

positioning a femoral alignment guide on a femur of a patient, the alignment guide at least partially conforming to the shape of the femur and positioned based on preoperatively acquired patient data such that the alignment guide simultaneously contacts the femur at least at nine points along an anterior to posterior curvature of the femur including at least three points on a non-resected medial femoral condyle, at least three points on a non-resected lateral femoral condyle and at least three points on a non-resected patellofemoral articular surface of the femur;

attaching at least one guide element through the alignment guide into an anterior, a medial, a distal or anterior medial surface of a distal end of the femur;

removing the alignment guide without removing the guide element;

supporting a femoral resection device on the at least one guide element after removing the alignment guide, the femoral resection device having a cutting tool guide surface having a shape matching at least a portion of an anterior periphery of a resected surface to be created on the femur;

preparing the femur to receive the orthopedic prosthesis by utilizing a cutting tool and using the femoral resection device to guide the cutting tool along the cutting tool guide surface to create the resected surface on a distal surface of the femur; and positioning the orthopedic prosthesis on the femur with the articulation surface of the orthopedic prosthesis aligned with the resected surface and disposing of the femoral alignment guide.

18. The method of claim 17, wherein the step of attaching the at least one guide element further includes the step of drilling resection location apertures into the unresected distal femoral condyles, wherein a second femoral resection device is operably attached to the resection location apertures after completion of the distal femoral cut and is used to create at least one of an anterior cut, an anterior chamfer cut, a posterior chamfer cut, and a posterior cut on the femur.

19. The method of claim 18, wherein the second femoral resection device is used to create the anterior cut, the anterior chamfer cut, the poster chamfer cut, and the posterior cut.

20. The method of claim 18, wherein the second femoral resection device is used to create the anterior cut and the posterior cut.

21. The method of claim 18, wherein the second femoral resection device is used to create the anterior chamfer cut and the posterior chamfer cut.

22. The method of claim 18, wherein at least one of the femoral resection device and the second femoral resection device is constructed of a polymer material.

* * * * *